(12) United States Patent
Fauver et al.

(10) Patent No.: US 11,878,499 B2
(45) Date of Patent: Jan. 23, 2024

(54) APPARATUS, SYSTEM, AND METHOD FOR ACTIVATING A LOW-ADHESION STATE OF THERMAL-SENSITIVE TAPE

(71) Applicant: University of Washington, Seattle, WA (US)

(72) Inventors: Mark E. Fauver, Seattle, WA (US); Eric J. Seibel, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 17/620,042

(22) PCT Filed: Jun. 26, 2020

(86) PCT No.: PCT/US2020/039815
§ 371 (c)(1),
(2) Date: Dec. 16, 2021

(87) PCT Pub. No.: WO2020/264291
PCT Pub. Date: Dec. 30, 2020

(65) Prior Publication Data
US 2022/0250374 A1    Aug. 11, 2022

Related U.S. Application Data

(60) Provisional application No. 62/868,739, filed on Jun. 28, 2019.

(51) Int. Cl.
*B32B 41/00* (2006.01)
*B32B 37/06* (2006.01)

(52) U.S. Cl.
CPC .............. *B32B 41/00* (2013.01); *B32B 37/06* (2013.01)

(58) Field of Classification Search
CPC ...... B32B 41/00; B32B 37/06; A61F 13/0253; A61F 13/0283; A61F 13/0289; A61F 13/0256
(Continued)

(56) References Cited

U.S. PATENT DOCUMENTS

| 5,156,911 A | 10/1992 | Stewart |
| 7,896,053 B2 | 3/2011 | Simandl et al. |

(Continued)

FOREIGN PATENT DOCUMENTS

| CN | 209111633 | 7/2019 |
| JP | 2015025932 | 2/2015 |

(Continued)

OTHER PUBLICATIONS

International Preliminary Report on Patentability dated Dec. 28, 2021, issued in corresponding International Application No. PCT/US2020/039815, filed Jun. 26, 2020, 7 pages.

(Continued)

*Primary Examiner* — Michael N Orlando
*Assistant Examiner* — Joshel Rivera
(74) *Attorney, Agent, or Firm* — Christensen O'Connor Johnson Kindness PLLC

(57) ABSTRACT

In some embodiments, an apparatus, system, and method for activating a low-adhesion state of a thermal-sensitive tape is described. An example apparatus embodiment includes a light source and a temperature sensor. The light source is configured to illuminate a target area of the thermal-sensitive tape with a first spectrum of electromagnetic radiation to provide heating of the target area. The first spectrum including a first wavelength outside of a visible spectrum. The temperature sensor is configured to detect a second spectrum of electromagnetic radiation to approximate a (Continued)

27 Claims, 18 Drawing Sheets

(58) Field of Classification Search
USPC .................. 156/60, 64, 350, 351, 378, 379
See application file for complete search history.

(56) References Cited

U.S. PATENT DOCUMENTS

| | | | |
|---|---|---|---|
| 8,323,250 | B2 | 4/2012 | Chong et al. |
| 8,946,499 | B2 | 2/2015 | Iyer et al. |
| 9,907,704 | B2 | 3/2018 | Laulicht et al. |
| 2004/0177918 | A1 | 9/2004 | Murata et al. |
| 2005/0037279 | A1 | 2/2005 | Miyako et al. |
| 2005/0277729 | A1 | 12/2005 | Tsunemine et al. |
| 2009/0081469 | A1 | 3/2009 | Oka et al. |
| 2009/0081849 | A1 | 3/2009 | Yamazaki et al. |
| 2012/0172949 | A1 | 7/2012 | Wagenaar Cacciola et al. |
| 2013/0084459 | A1 | 4/2013 | Larson et al. |
| 2017/0308980 | A1 | 10/2017 | Desai et al. |
| 2018/0014734 | A1 | 1/2018 | Rogers et al. |
| 2018/0353640 | A1 | 12/2018 | Seibel et al. |

FOREIGN PATENT DOCUMENTS

| | | |
|---|---|---|
| JP | 2015059154 | 3/2015 |
| JP | 2016138182 | 8/2016 |
| JP | 2019203054 | 11/2019 |
| KR | 20200020114 | 2/2020 |
| TW | 453862 | 9/2001 |
| TW | 200418949 | 10/2004 |
| TW | 200524997 A | 8/2005 |
| TW | 201945489 | 12/2019 |
| TW | 201946994 | 12/2019 |
| WO | 1997/012561 A2 | 4/1997 |
| WO | 2017091515 A1 | 6/2017 |

OTHER PUBLICATIONS

ASTM, 1999, "Standard Guide for Heated System Surface Conditions That Produce Contact Burn Injuries," Annual Book of ASTM Standards, vol. 04.06, West Conshohocken, PA, Standard No. ASTM-C1055-99.
ASTM, 2018, "Standard Test Method for Peel Adhesion of Pressure-Sensitive Tape," ASTM, West Conshohocken, PA, Standard No. D3330/D3330M-04.
Chivers, Robin A. "Easy removal of pressure sensitive adhesives for skin applications." International journal of adhesion and adhesives 21.5 (2001): 381-388.
FDA, "CFR—Code of Federal Regulations Title 21," vol. 8, 21CFR880. 5240, <https://www.accessdata.fda.gov/scripts/cdrh/cfdocs/cfcfr/CFRSearch.cfm?FR=880.5240> [Retrieved Jul. 18, 2022], 2 pages.
Gao, Ge, et al. "Near-infrared light-controllable on-demand antibiotics release using thermo-sensitive hydrogel-based drug reservoir for combating bacterial infection." Biomaterials 188 (2019): 83-95.
Laulicht, Bryan, Robert Langer, and Jeffrey M. Karp. "Quick-release medical tape." Proceedings of the National Academy of Sciences 109.46 (2012): 18803-18808.
Xu, Xiaomo, et al. "Controlled-temperature photothermal and oxidative bacteria killing and acceleration of wound healing by polydopamine-assisted Au-hydroxyapatite nanorods." Acta biomaterialia 77 (2018): 352-364.
Lim et al., "Proof of Concept of a Surrogate High-Adhesion Medical Tape Using Photo-Thermal Release for Rabid and Less Painful Removal," Journal of Medical Devices vol. 14/021001, Jun. 1-11, 2020.
United States Food and Drug Administration Department of Health and Human Services, 2017, "Code of Federal Regulations Title 21, Section 880.5240: Medical Adhesive Tape and Adhesive Bandage," United States Food and Drug Administration Department of Health and Human Services, Silver Spring, MD, Standard No. 21CFR880. 5240.
Van Schaik, R., and Rovekamp, M. H., 2011, "Fact or Myth? Pain Reduction in Solvent-Assisted Removal of Adhesive Tape," J. Wound Care, 20(8), pp. 380-383.
McNichol, L., Lund, C., Rosen, T., and Gray, M., 2013, "Medical Adhesives and Patient Safety: State of the Science: Consensus Statements for the Assessment, Prevention, and Treatment of Adhesive-Related Skin Injuries," J. Dermatol. Nurses. Assoc., 5(6), pp. 323-338.
Zhao, H., He, Y., Huang, H., Ling, Y., Zhou, X., Wei, Q., Lei, Y., and Ying, Y., 2018, "Prevalence of Medical Adhesive-Related Skin Injury at Peripherally Inserted Central Catheter Insertion Site in Oncology Patients," J. Vasc. Access, 19(1), pp. 23-27.
Ratliff, C. R., 2017, "Descriptive Study of the Frequency of Medical Adhesive-Related Skin Injuries in a Vascular Clinic," J. Vasc. Nurs., 35(2), pp. 86-89.
Ousey, K., Cooper, K., Fumarola, S., and Hitchcock, J., 2017, "Findings From a Multidisciplinary Focus Group Meeting to Discuss the Issue of Medical Adhesive-Related Skin Injury (MARSI) in the UK: The Way Forward," Wounds UK, 13(4), pp. 141-145.
Wang, D., Xu, H., Chen, S., Lou, X., Tan, J., and Xu, Y., 2019, "Medical Adhesive-Related Skin Injuries and Associated Risk Factors in a Pediatric Intensive Care Unit," Adv. Skin Wound Care, 32(4), pp. 176-182.
Farris, M. K., Petty, M., Hamilton, J., Walters, S.- A. A., and Flynn, M. A., 2015, "Medical Adhesive-Related Skin Injury Prevalence Among Adult Acute Care Patients," J. Wound, Ostomy Continence Nurses, 42(6), pp. 589-598.
Ullman, A. J., Kleidon, T., Gibson, V., McBride, C. A., Mihala, G., Cooke, M., and Rickard, C. M., 2017, "Innovative Dressing and Securement of Tunneled Central Venous Access Devices in Pediatrics: A Pilot Randomized Controlled Trial," BMC Cancer, 17(1), p. 595.
Taroc, A.-M., 2015, "Staying Out of Sticky Situations: How to Choose the Right Tape for Your Patient," Wound Care Advis., 4(6), pp. 21-26.
Manriquez, S., Loperfido, B., and Smith, G., 2014, "Evaluation of a New Silicone Adhesive Tape Among Clinicians Caring for Patients With Fragile or At-Risk Skin," Adv. Ski. Wound Care, 27(4), pp. 163-170.
De Crevoisier, G., Fabre, P., Corpart, J. M., and Leibler, L., 1999, "Switchable Tackiness and Wettability of a Liquid Crystalline Polymer," Science, 285(5431), pp. 1246-1249.
Kamperman, M., and Synytska, A., 2012, "Switchable Adhesion by Chemical Functionality and Topography," J. Mater. Chem., 22(37), pp. 19390-19401.
Boyne, J., Millan, E., and Webster, I., 2001, "Peeling Performance of a Novel Light Switchable Pressure-Sensitive Adhesive," Int. J. Adhes. Adhes., 21(1), pp. 49-53.
Clearweld, 2011, "Clearweld 900 Series Product Guide," Gentex Corporation, Carbondale, PA, accessed Nov. 6, 2019, http://www.clearweld.com/cms-assets/documents/Clearweld_900_Series_Coatings_Guide-web.pdf.
Klein, R., 2012, Laser Welding of Plastics: Materials, Processes and Industrial Applications, Wiley, Hoboken, NJ.
Yarnitsky, D., Sprecher, E., Zaslansky, R., and Hemli, J. A., 1995, "Heat Pain Thresholds: Normative Data and Repeatability," Pain, 60(3), pp. 329-332.
Martin, N. A., and Falder, S., 2017, "A Review of the Evidence for Threshold of Burn Injury," Burns, 43(8), pp. 1624-1639.
Dewey, W. C., 2009, "Arrhenius Relationships From the Molecule and Cell to the Clinic," Int. J. Hyperth., 25(1), pp. 3-20.
Diller, K. R., 2006, "Adapting Adult Scald Safety Standards to Children," J. Burn Care Res., 27(3), pp. 314-322.
ASTM, 2010, "Standard Test Method for Peel Adhesion of Pressure-Sensitive Tape," ASTM, West Conshohocken, PA, Standard No. D3330/D330M.
Okabe, T., Fujimura, T., Okajima, J., Aiba, S., and Maruyama, S., 2018, "Non-Invasive Measurement of Effective Thermal Conduc-

(56) References Cited

OTHER PUBLICATIONS tivity of Human Skin With a Guard-Heated Thermistor Probe," Int. J. Heat Mass Transfer, 126, pp. 625-635.
Lumileds Holding B.V., 2018, "LUXEON IR Domed Line Specification Data," Lumileds Holding B.V., San Jose, CA, accessed Nov. 6, 2019, https://www.lumileds.com/uploads/685/DS191-pdf.
Okada, T., Ishige, R., and Ando, S., 2016, "Analysis of Thermal Radiation Properties of Polyimide and Polymeric Materials Based on ATR-IR Spectroscopy," J. Photopolym. Sci. Technol., 29(2), pp. 251-254.
Weinstein, S., and Hagle, M. E., 2014, Plumer's Principles & Practice of Infusion Therapy, Lippincott Williams & Wilkins, Philadelphia, PA, pp. 320-321.
Henriques, F. C., 1947, "Studies of Thermal Injury—V: The Predictability and the Significance of Thermally Induced Rate Processes Leading to Irreversible Epidermal Injury," Am. J. Pathol., 43(5), pp. 489-502.
ASTM, 2014, "Standard Guide for Heated System Surface Conditions that Produce Contact Burn Injuries," ASTM, West Conshohocken, PA, Standard No. ASTM-C1055-03.
Moon et al., "Evaluation of temperature-dependent adhesive performance via combinatorial probe tack measurements," Feb. 2005, https://aip.scitation.org/doi/abs/10.1063/1.1906105.
Stokes-Griffin et al., "A combined optical-thermal model for near-infrared laser heating of thermoplastic composites in an automated tape placement process," Aug. 2015, https://www.sciencedirect.com/science/article/abs/pii/S1359835X14002395.
Stansbury et al., "Determination of double bond conversion in dental resins by near infrared spectroscopy," Jan. 2001, https://www.sciencedirect.com/science/article/abs/pii/S0109564100000622.
Kajtna et al., The influence of the polymerization on properties of an ethylacrylate/2-ethyl hexylacrylate pressure-sensitive adhesive suspension, International Journal of Adhesion and Ashesives, vol. 28, Issue 7, Oct. 2008, pp. 382-390.
Kajtna et al., "The Role of Components in Waterbased Microsphere Acrylic Psa Adhesive Properties," Dec. 20, 2006, Mactromelecular Symposia 243(1): 132-146.
Zhang et al., "Repositionable pressure-sensitive adhesive possessing thermal-stimuli switchable transparency," Journal of Materials Chemistry C, Issue 6, 2013.
Hilton et al., "Laser Welding of Fabrics Using Infrared Absorbing Dyes," International Conference on Joining of Advanced and Specialty Materials III ASM 2000, Oct. 9-12, 2000, 6 pages.
Svanevik, "Testing and Improving the UnTape Medical Device Concept," University of Washington, 2018, 91 pages.
International Patent Application No. PCT/US2020/039815—International Search Report and Written Opinion, dated Sep. 11, 2020, 10 pages.

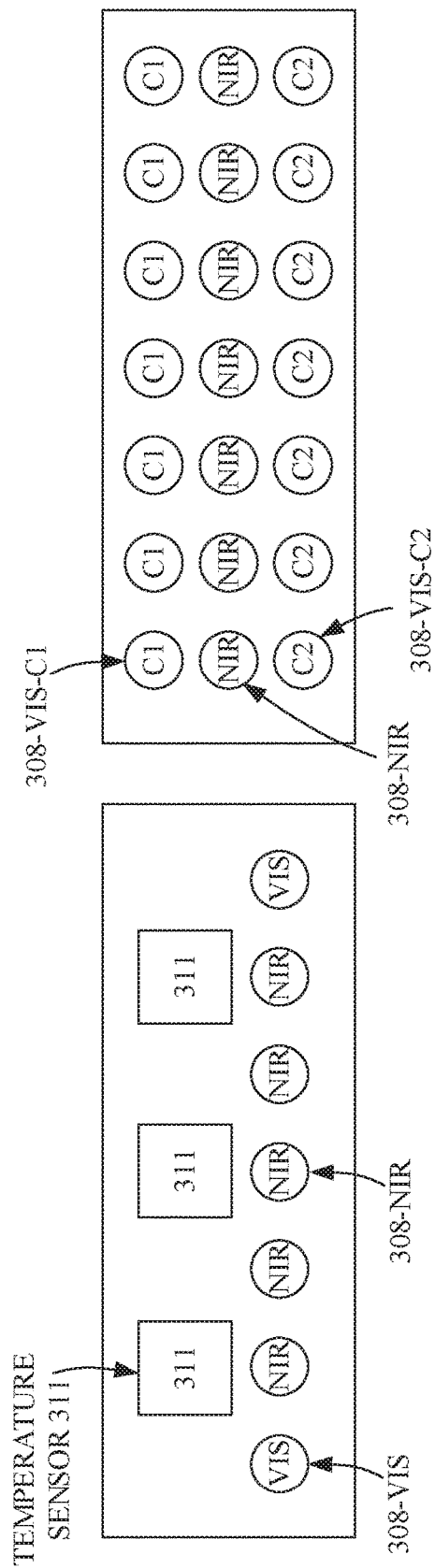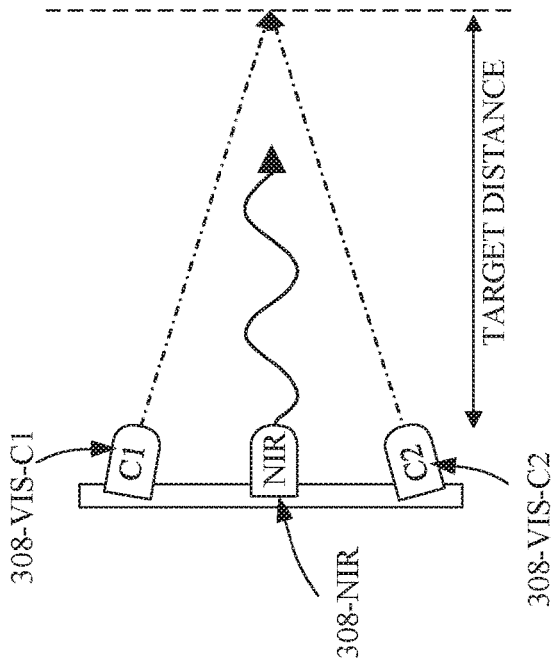
FIG. 3F
FIG. 3G
FIG. 3D
FIG. 3E

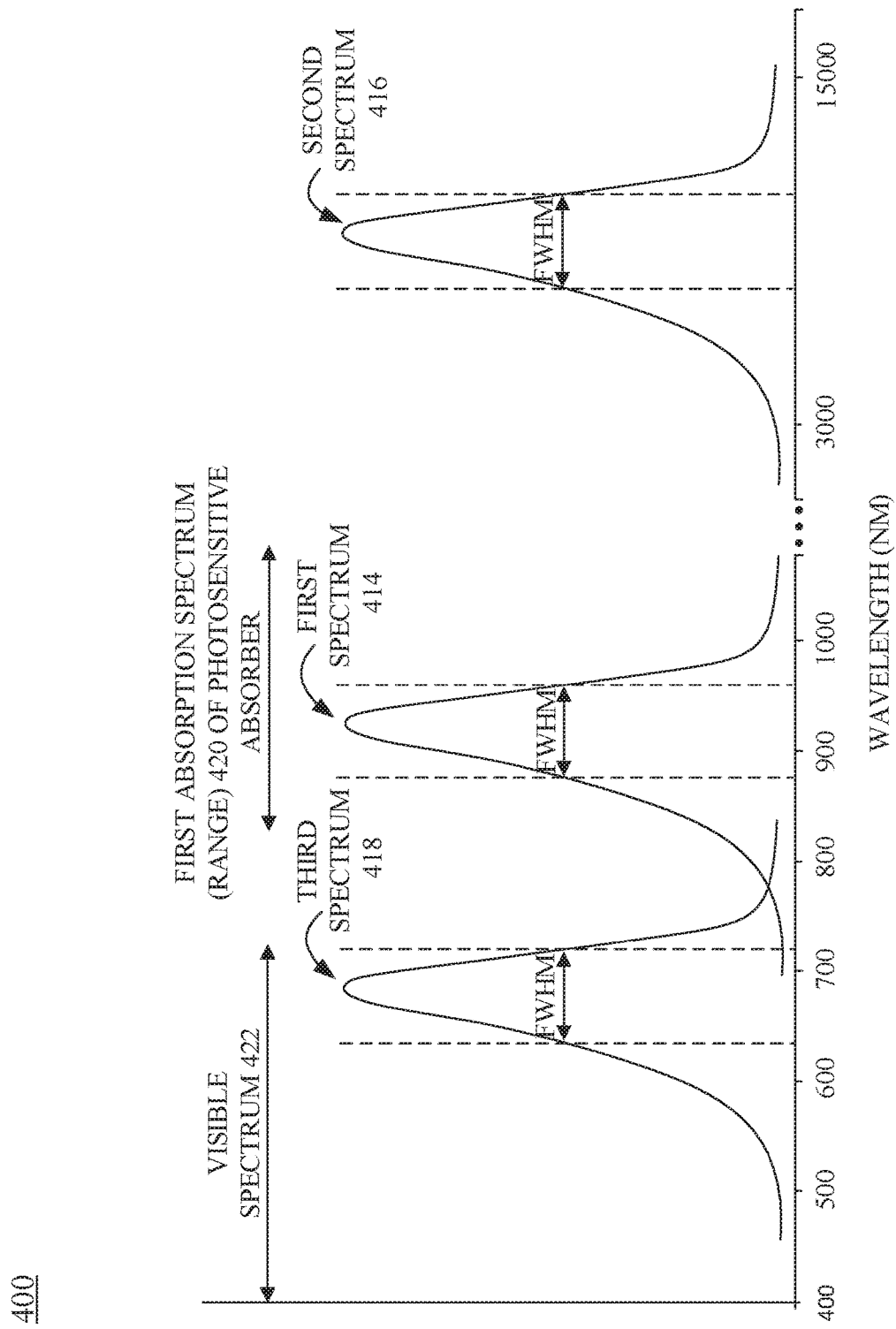

United States Patent US 11,878,499 B2

APPARATUS, SYSTEM, AND METHOD FOR ACTIVATING A LOW-ADHESION STATE OF THERMAL-SENSITIVE TAPE

CROSS-REFERENCE TO RELATED APPLICATION

This application is a national stage application, filed under 35 U.S.C. § 371, of International Patent Application No. PCT/US2020/039815 filed Jun. 26, 2020, which claims the benefit of U.S. Provisional Patent Application No. 62/868,739, filed on Jun. 28, 2019, each of which is hereby expressly incorporated by reference in its entirety.

BACKGROUND

Medical adhesive tapes are a class of ubiquitous medical devices with a plastic or fabric backing, coated on one side with an adhesive layer. According to the FDA Code of Federal Regulations Title 21 Section 880.5240, "the device is used to cover and protect wounds, to hold together the skin edges of a wound, to support an injured part of the body, or to secure objects to the skin." Adhesion to the skin is the primary objective of these functions. However, a stronger and more stable adhesive bond to the skin requires a more laborious and often painful removal process, which can lead to anxiety for patient and caregiver and medical adhesive-related skin injuries (MARSIs).

MARSI is defined as an occurrence of erythema or cutaneous abnormality (including blister, erosion, tear, etc.) that persists 30 minutes or more after adhesive removal. The prevalence rates of MARSI vary significantly between studies for patient populations and the type and location of the medical adhesive. One study reported a total MARSI incidence of 29.83% at the peripherally inserted central catheter insertion sites of oncology patients. Another study reported a MARSI incidence of 5.8% with 207 patient visits in an outpatient vascular clinic over 3 months. MARSI is potentially underreported in many areas of care, as it is not considered an unexpected or adverse injury. From one study in a pediatric intensive care unit, 76.3% of MARSI was caused by the securements of tracheal intubation, vascular access, and electrocardiogram monitor. Because accidental dislocation of those critical medical devices can result in serious events, the problems resulting from limited choices in medical tape are expected to be well beyond MARSI prevalence. Although the probability of MARSI is based on the combination of various risk factors, it is highest with neonatal patients, as neonatal skin is nearly 50% thinner than adult skin, and with geriatric patients who often have compromised skin. In a study published in 2015, the daily MARSI prevalence ranged from 3.4% to 25.0% with a mean of 13.0% and a patient median age of 58 years. In a pilot study with pediatric patients who required central venous access devices secured by clear medical tape, skin injuries were a substantial issue affecting 9% of patients and causing an additional 4% to withdraw due to skin irritation.

In the U.S., nurses are aware of MARSI risk and take responsibility for choosing the type of medical tape needed for the patient given the specific task required. To reduce the incidence of MARSI, 3M™ introduced a silicone-based adhesive tape for patients most at risk of MARSI. This was compared to standard acrylate-based plastic tape over a two-week period by over 200 nurses. More than half of the nurses surveyed were dissatisfied with the current tapes when used on patients with fragile or at-risk-skin. Unlike the acrylate-based adhesives, which have higher skin adhesion over time, the silicone-based adhesive remains consistent over time, but adherence may be unreliable with silicone products or critical tubing. As such, low tack and low adhesion silicone adhesives that provide easy and rapid removal should not be used in the securement of central or peripheral venous catheters even for neonatal and geriatric patients. To obtain high initial tack and strong skin adhesion, chemical solvents are used to slowly remove the adhesive to avoid the increased risk of damaging the epidermal layer of the skin. Tape selection based on the patient's condition and clinical need is crucial as current single adhesive products do not serve a wide range of situations.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, an apparatus for activating a low-adhesion state of a thermal-sensitive tape is described. The apparatus comprising a light source and a temperature sensor. The light source is configured to illuminate a target area of the thermal-sensitive tape with a first spectrum of electromagnetic radiation to provide heating of the target area. The first spectrum including a first wavelength outside of a visible spectrum. The temperature sensor is configured to detect a second spectrum of electromagnetic radiation to approximate a temperature of the target area. The second spectrum including a second wavelength different than the first wavelength.

In another aspect a system comprising a thermal-sensitive tape and an apparatus is described. The thermal-sensitive tape including a photosensitive absorber that absorbs incident light within a first absorption spectrum of electromagnetic radiation, wherein adhesive strength of a target area of the thermal-sensitive tape is based on a temperature of the target area. The apparatus is configurable to illuminate the target area of the thermal-sensitive tape and includes a light source, a temperature sensor, and an indicator light. The light source is configured to illuminate the target area of the thermal-sensitive tape with a first spectrum of electromagnetic radiation to provide heating of the target area. The first spectrum includes a first wavelength outside of a visible range spectrum. The first spectrum overlaps, at least in part, with the first absorption spectrum such that the temperature of the target area is based, at least in part, on an intensity of the first spectrum output by the light source when the light source is illuminating the target area. The temperature sensor is configured to detect a second spectrum of electromagnetic radiation to approximate a temperature of the target area. The second spectrum includes a second wavelength different than the first wavelength. The indicator light is configured to illuminate the target area with a third spectrum of electromagnetic radiation to visually indicate a location of the heating. The third spectrum including a third wavelength within the visible spectrum.

In yet another aspect, a method for activating a low-adhesion state of a thermal-sensitive tape is described. The method comprising illuminating a target area of the thermal-sensitive tape with a first spectrum of electromagnetic radiation to provide heating of the target area of the thermal-sensitive tape to within a thermal release temperature range. The first spectrum including a first wavelength outside of a visible spectrum. The method further comprising monitoring a temperature of the target area by detecting a second spectrum of electromagnetic radiation emitted by the thermal-sensitive tape to provide temperature feedback. The method additionally comprising illuminating the target area of the thermal-sensitive tape with a third spectrum of electromagnetic radiation to visually indicate a location of the heating. The third spectrum including a third wavelength within the visible spectrum. The method further comprising adjusting an intensity of the first spectrum based on the temperature feedback to maintain the temperature of the target area within the thermal release temperature without exceeding a first threshold temperature.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 3D-3G illustrate various non-limiting example arrangements of a plurality of light emitting diodes and temperature sensor, in accordance with an embodiment of the disclosure.

FIG. 4 illustrates a chart showing relative position in terms of wavelength for a first spectrum of electromagnetic radiation, a second spectrum of electromagnetic radiation, a third spectrum of electromagnetic radiation, a visible spectrum, and a first absorption spectrum range, in accordance with embodiments of the disclosure.

DETAILED DESCRIPTION

Figure 1A:
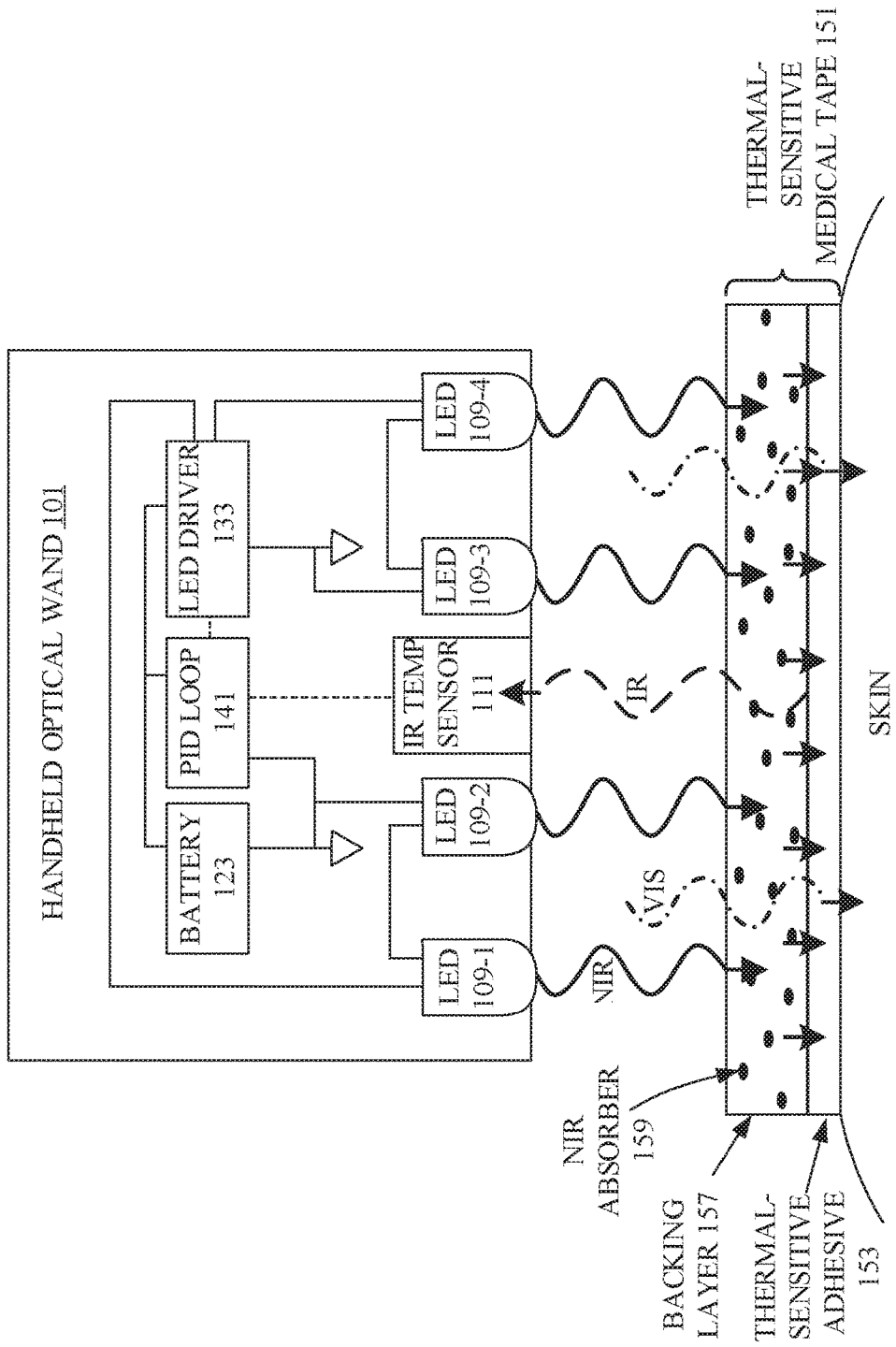
FIG. 1A illustrates a system including a handheld optical wand and a thermal-sensitive medical tape 151 contacting skin, in accordance with embodiments of the disclosure.

Embodiments of an apparatus, system, and method for activating a low-adhesion state of thermal-sensitive tape without temperature overshoot is described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Some portions of the detailed description that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "receiving", "providing", "estimating", "determining", "verifying", "monitoring", "generating", "identifying", "adjusting", "calculating", "simulating", "aborting", or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such as information storage, transmission, or display devices.

The algorithms and displays presented herein are not inherently related to any particular computer or other apparatus. Various general purpose systems may be used with programs in accordance with the teachings herein, or it may prove convenient to construct a more specialized apparatus to perform the required method steps. The required structure for a variety of these systems will appear from the description below. In addition, embodiments of the present disclosure are not described with reference to any particular programming language. It will be appreciated that a variety of programming languages may be used to implement the teachings of the disclosure as described herein.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Accordingly, it will be readily understood aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood other embodiments may include more or less of each element shown in a given Figure. Further, some of the illustrated elements may be combined or omitted. Yet further, an example embodiment may include elements not illustrated in the Figures. As used herein, with respect to measurements, ranges, and the like, the terms "about" and "approximately" means ±5%.

FIG. 1A illustrates a system 100 including a handheld optical wand 101 and a thermal-sensitive medical tape 151 contacting skin, in accordance with embodiments of the disclosure. Handheld optical wand 101 includes a plurality of light emitting diodes 109 (e.g., near-infrared emitters), one or more infrared temperature sensors 111, a battery 123, an LED driver 133, and a PID loop. Thermal-sensitive medical tape 151 includes a thermal-sensitive adhesive 153, a backing layer 157, and a near-infrared ("NIR") absorber 17 distributed throughout the backing layer. Thermal-sensitive medical 151 has variable tack strength (e.g., adhesion strength when affixed to skin) dependent, at least in part, on an instantaneous temperature of the thermal-sensitive medical tape to enable easier removal, detachment, or otherwise decouple at least part of the thermal-sensitive medical tape 151 from an object (e.g., human skin in the context of a medical application).

As illustrated, FIG. 1A shows generally the interaction of the components of system 100, and further shows an embodiment where the NIR absorber 159 is integrated (or coated on) the backing layer 157. The handheld optical wand 101 emits near-infrared light (e.g., via plurality of LEDs 109). Heat is generated from the absorption of the NIR light by the NIR absorbers 159 and then that heat radiates or otherwise conducts throughout the thermal-sensitive medical tape 151 to the thermal-sensitive adhesive 153. The temperature of the thermal-sensitive medical tape 151 is monitored via an infrared ("IR") temperature sensor 111 (e.g., determined by blackbody radiation emitted by the thermal-sensitive medical tape 151) simultaneously (e.g., at the same time the plurality of LEDs 109 are emitting NIR light) to generate temperature feedback (e.g., temperature data representative of the temperature of the thermal-sensitive medical tape 151, the underlying skin, any interlayers, or combinations thereof) More specifically, the temperature data is fed into a PID control loop 141, which regulates (e.g., via pulse width modulation) of the NIR light output by the plurality of LEDs 109 such that the temperature of the thermal-release medical tape 151 and the underlying skin does not exceed a first threshold (e.g., a pain threshold temperature), but is increased to and maintained within a thermal release temperature range for a long enough duration to switch the thermal-sensitive adhesive 153 from a high-adhesion state to a low-adhesion state to enable easier removal of the thermal-sensitive medical tape 151 from the skin. In some embodiments, the backing layer 157 and the thermal-sensitive adhesive 153 are at least partially transmissive to visible light so the status of the underlying wound, which may be bleeding and/or infected in some cases) can be assessed while the thermal-sensitive medical tape 151 is adhered to the skin.

Figure 1B:
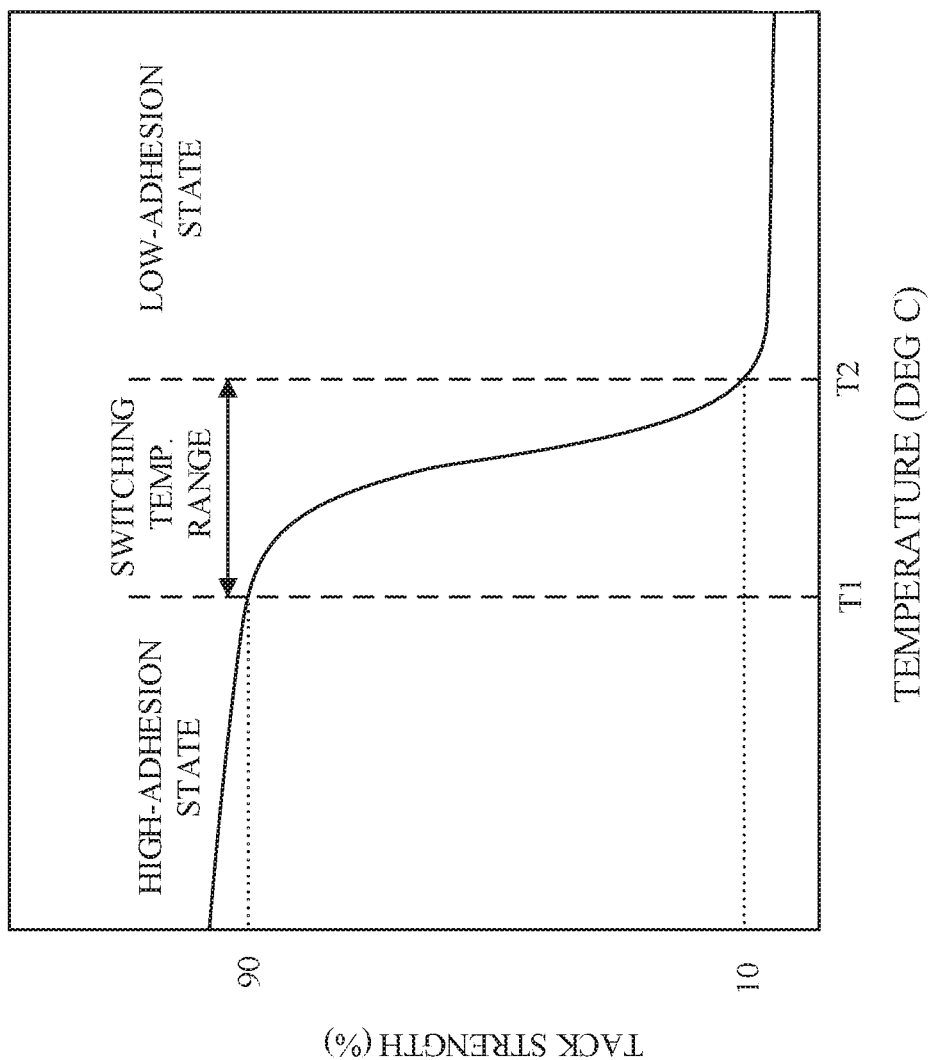
FIG. 1B illustrates a non-limiting diagram describing tack strength (e.g., adhesion strength) of the thermal-sensitive adhesive included in thermal-sensitive medical tape illustrated in FIG. 1A, in accordance with an embodiment of the disclosure.

FIG. 1B illustrates a non-limiting diagram describing tack strength (e.g., adhesion strength) of the thermal-sensitive adhesive 153 included in thermal-sensitive medical tape 151 illustrated in FIG. 1A, in accordance with an embodiment of the disclosure. As illustrated in FIG. 1B, the thermal-sensitive adhesive 153 is considered in a high-adhesion state when at a temperature below a first temperature, T1, and in a low-adhesion state when at a temperature above T2. The tack strength or adhesion strength may vary considerably between the low- and high-adhesion states. For example, as illustrated the high-adhesion state is approximately nine times greater than the low-adhesion state of the thermal-sensitive adhesive 153. It is appreciated that in some embodiments, any temperature greater than T1 is within a thermal-release temperature range of the thermal-sensitive adhesive 153 (and thus consequently the thermal-sensitive medical tape 151). Any temperature between T1 and T2 is within a switching temperature range, which may be utilized for fine adjustment of tack strength. It is further appreciated that in some embodiments, the thermal-sensitive medical tape 151 is considered to be in a high-adhesion state when the temperature is below T1 and in a low-adhesion state for any temperature above T1. Thus, in some embodiments, the low-adhesion state may encompass the entire variable range of adhesion of the thermal-sensitive medical tape 151. In other words, the low-adhesion state may be generally referred to as a state of the thermal-sensitive medical tape 151 that has a lower adhesion strength relative to an initial adhesion strength (e.g., max adhesion strength) when the thermal-sensitive medical tape 151 was originally affixed to an object. Thus, activation of the low-adhesion state may generally be induced by increasing the temperature of the thermal-sensitive medical tape 151 (or more specifically thermal-sensitive adhesive 153), at least temporarily, to a temperature above T1.

In some embodiments the thermal-release switching temperature range (e.g., the difference between T1 and T2) is approximately 10° C. For example, in one embodiment, T1 is approximately 35° C. and T2 is approximately 45° C. In other embodiments, T1 is approximately 40° C. and T2 is approximately 50° C. It is appreciated that examples of T1 and T2 should not be deemed limiting and that the thermal-sensitive adhesive 153 in the thermal-sensitive medical tape 151 may be configured as necessary to support a target switching temperature range dependent upon application. For example, in a thermal-sensitive medical tape application, where skin temperature is approximately 33° C. to 37° C., the thermal-sensitive adhesive 153 may be configured such that T1 is approximately 39° C. and T2 is approximately 42° C. In such an embodiment, fine temperature adjustment may be utilized to control the adhesion strength dependent on a pain threshold of the invention and how fast removal of the thermal-adhesive 153 is targeted. For example, the first threshold temperature (e.g., temperature set point of the apparatus 101) could be T1, T2, any temperature between T1 and T2, or otherwise.

Referring back to FIG. 1A, embodiments of system 100 (and other embodiments described throughout the disclosure) enable release of thermal sensitive-medical tape 151 with thermal-sensitive adhesive 153 without risk of pain or injury to the patient. The system 100 employs active feedback control, allowing the rate of energy delivered to the thermal-sensitive medical tape 151 to be maximized (e.g., fastest release of the tape) without exceeding past a first threshold temperature (e.g., a pain threshold at a temperature of 45° C.). Fine control of the upper temperatures of the thermal-sensitive medical tape 151 reached by applying energy via the handheld optical wand 101 is important because, in some embodiments, the switching temperature range for the thermal-sensitive adhesive 153 may be as low as 10° C. which may be comparable to the different between skin temperature (e.g., 34° C.) and the temperature of the pain threshold (e.g., 45° C.).

It is appreciated that though system 100 (and other embodiments of the disclosure) is generally directed towards medical applications in which the thermal-sensitive medical tape 151 is adherable to skin, other applications where temporarily fixing any object to skin may be desirable will also see a benefit from the use of the apparatus, system, and methods described herein. For example, non-medically related applications such as cosmetic or athletic tapes, healthcare products, wearable sensors, and the like. Furthermore, it is noted embodiments described herein are not limited to removably affixing objects to skin. Rather, the present embodiments may provide advantages to any situation in which variable adherence between two objects is desired without exceeding one or more threshold temperatures.

Figure 2:
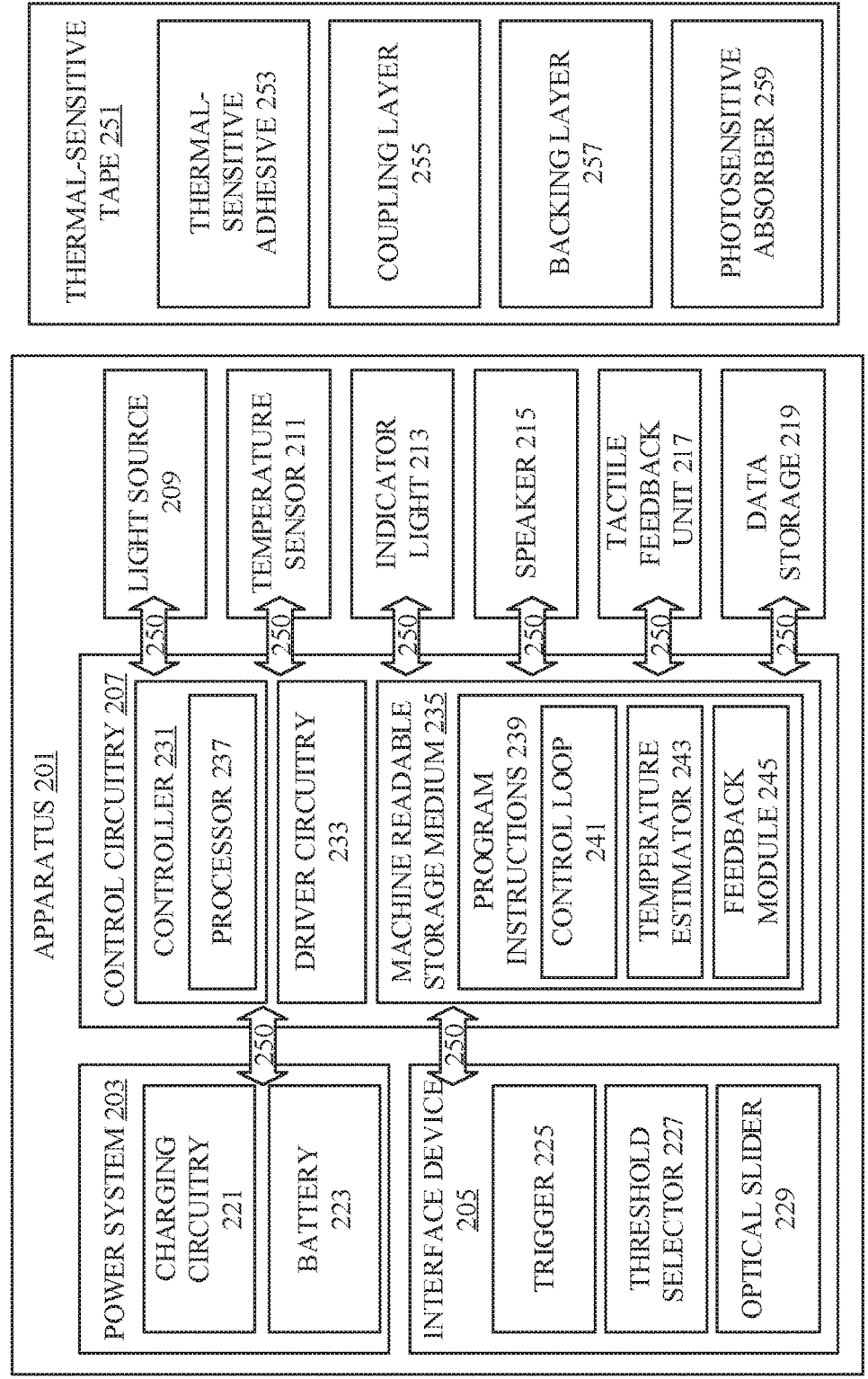
FIG. 2 illustrates a functional block diagram of a system including an apparatus and a thermal-sensitive tape, in accordance with an embodiment of the disclosure.

FIG. 2 illustrates a functional block diagram of a system 200 including an apparatus 201 and a thermal-sensitive tape 251, in accordance with an embodiment of the disclosure. System 200 is one possible system that may implement system 100 illustrated in FIG. 1A. For example, apparatus 201 (e.g., optical wand 101 of FIG. 1A) is capable of activating a low-adhesion state of thermal-sensitive tape 251 (e.g., thermal-sensitive tape 151 of FIG. 1A).

In the depicted embodiment of FIG. 2, apparatus 201 includes power system 203, one or more interface devices 205, control circuitry 207, one or more light sources 209 (e.g., a light emitting diode, laser diode, or other emissive element configured to emit a first spectrum of electromagnetic radiation, including a first wavelength outside of a visible spectrum, to provide heating of the thermal-sensitive tape 251), one or more temperature sensors 211 (e.g., pyrometer or other sensor configured to detect a second spectrum of electromagnetic radiation to approximate a temperature of the thermal-sensitive tape 251), one or more indicator lights 213 (e.g., a light emitting diode, laser diode, or other emissive element configured to emit a third spectrum of electromagnetic radiation, including a third wavelength within the visible spectrum) to visually indicate a location of the heating of heating), one or more audio speakers 215, one or more tactile feedback units 217 (e.g., vibration based unit such as an eccentric rotating mass actuator, linear resonant actuator, or the like), and data storage 219. The power system 203 includes charging circuitry 221 and battery 223. The one or more interface devices 205 include an initialization trigger 225, a threshold selector 227, and an optical slider 229. The control circuitry 207 includes control 231, driver circuitry 233, and machine readable storage medium 235. The controller 231 includes one or more processors 237 (e.g., application specific processor, field-programmable gate array, central processing unit, microcontroller, and/or a combination thereof). The machine readable storage medium 235 includes program instructions 239, which includes a control loop 241, a temperature estimator 243, and feedback module 245. Each of the components of apparatus 201 may be coupled (e.g., electrically) to one another via interconnects 250.

The power system 203 provides operating voltages to the interface devices 205, control circuitry 207, temperature sensor 211, indicator light 213, speaker 215, tactile feedback unit 217, data storage 219, and any other component of apparatus 201 via battery 223 (e.g., alkaline, lithium ion, one or more capacitors, and any other energy storage unit). In some embodiments, battery 223 may be replaceable and/or rechargeable in which charging circuitry provides the necessary components to interface with an external power source to recharge battery 223 upon depletion of charge.

The one or more interface devices 205 enable a user to activate operation, terminate operation, and/or various configure parameters of apparatus 201. Trigger 225 is a depressible mechanism (e.g., spring loaded button, switch, lever, or the like) that when depressed activates apparatus 201 (e.g., causes the apparatus 201 to perform operations including illuminating a target area with any one of light source 209, indicator light 213, or combinations thereof, sense temperature of the target are with the temperature sensor 211, or the like). Upon release of trigger 225, apparatus 201 may cause output operations (e.g., stop illuminating the target area). Threshold selector 227 may be one or more sliders, buttons, switches, or otherwise to enable the user to configure various operational thresholds of apparatus 201 (e.g., first threshold temperature, second threshold temperature, thermal release temperature range, or the like) based on a user preference. Optical slider 229 may be mechanical (automated or otherwise) slider configured to variably block the output of apparatus 201 (e.g., to control a width, length, or other shape of the beam of illumination output by the one or more light sources, indicator lights 213, or combinations thereof).

The control circuitry 207 includes the controller 231 coupled to driver circuitry 233 and machine readable storage medium 235. The driver circuitry 233 includes circuitry for driving the one or more light sources 209 and indicator lights 213. The machine readable storage medium 235 includes program instructions 239 that when executed by the controller 231 causes the apparatus 201 to perform operations. The program instructions 235, for example, may choreograph operation of the components of apparatus 201 for activating a low-adhesion state of thermal-sensitive tape 251 without temperature overshoot (e.g., without a target area of the thermal-sensitive tape 251 exceeding a first and/or second threshold). In some embodiments, control loop 241 may provide instructions for repeatedly adjusting illumination on a target area of the thermal-sensitive tape 251 in response to temperature feedback. Temperature estimator 243 may provide instructions for estimating a temperature of the target area based on an output of temperature sensor 211 and/or calculate an underlying temperature of an object adhered to the thermal-sensitive tape 251. Feedback module 245 may provide instructions for generating feedback in response to one or more detected events (e.g., changing output color of the one or more indicator lights 213, activating an audio cue with speaker 215, or generating a vibratory notification via tactile feedback unit 217 to indicate to a user of the apparatus that the temperature of the target area is within a thermal release temperature range or otherwise. Data storage 219 may be a storage medium for logging operation of apparatus 201.

It is appreciated that the data storage 219 and machine readable storage medium 235 are non-transitory machine-readable storage mediums that may include, without limitation, any volatile (e.g., RAM) or non-volatile (e.g., ROM) storage system readable by components of system 200. It is further appreciated that system 200 may not show all logic modules, program instructions, or the like. All of which may be implemented in software/firmware executed on a general purpose microprocessor, in hardware (e.g., application specific integrated circuits), or a combination of both.

Thermal-sensitive tape 251 includes thermal-sensitive adhesive 253 (e.g., any adhesive with a variable tack strength or adhesion strength based on temperature such as Intelimer® Tape, manufactured by Nitta Corporation under license from the Landec Corporation), an optional coupling layer 255 (e.g. a sacrificial intermediate layer including one or more components having adhesive properties such as an acrylic adhesive), a backing layer 257 (e.g., one or more polymers having target transmissive properties while maintaining structure to provide form to the thermal-sensitive tape 251), and one or more photosensitive absorbers 259 (e.g., NIR absorber, NIR absorbing dye, NIR absorbing molecule, or the like such as LD920C Clearweld®, manufactured by Gentex Corporation). In some embodiments, the photosensitive absorber 259 may be disposed as a layer on the coupling layer 255, the backing layer 257, or combinations thereof. In the same or other embodiments, the photosensitive absorber 259 may be distributed uniformly, randomly, or otherwise integrated into the coupling layer 255, the backing layer 257, or combinations thereof. Additionally, in the same or other embodiments, the thermal-sensitive adhesive 253 may be disposed on an outermost layer of the thermal-sensitive tape 251 such that the thermal-sensitive adhesive 253 may be positioned in direct contact with an object (e.g., human skin).

In one embodiment, the light source 209 is configured to illuminate a target area of the thermal-sensitive 251 tape with the first spectrum of electromagnetic radiation. In some embodiments, the first spectrum of electromagnetic radiation is selected from between 750 nm and 1750 nm, between 750 nm and 1000 nm, or any other ranges sufficient to be absorbed by the photosensitive absorber 259 to provide heating of the target area of the thermal-sensitive 251. In some embodiments the first spectrum includes a first wavelength outside of a visible spectrum. The visible spectrum is defined as approximately 400 nm to 700 nm. Thus, in one embodiment, the first wavelength of the first spectrum of electromagnetic radiation is not within the range of 400 nm to 700 nm. In one embodiment, the first wavelength is approximately 940 nm. In the same or other embodiments, the temperature sensor 211 is configured to detect a second spectrum of electromagnetic radiation. In some embodiments, the second spectrum of electromagnetic radiation is selected from between 3 µm and 15 µm, between 5 µm and 14 µm, or any other range sufficient to approximate a temperature of the target area in a contactless manner to provide temperature feedback for the heating. In some embodiments, the second spectrum includes a second wavelength different than the first wavelength. In one embodiment, the second wavelength is approximately 5 µm. In one or more embodiments, the indicator light 213 is configured to illuminate the target area with a third spectrum of electromagnetic radiation that is within the visible spectrum. In other words, in certain embodiments the third spectrum is within approximately 400 nm to 700 nm of electromagnetic radiation to visually indicate a location of the heating and includes a third wavelength within the visible spectrum different from the second wavelength.

As illustrated, the photosensitive absorber 259 is capable of absorbing incident light within a first absorption spectrum of electromagnetic radiation. The first spectrum overlaps, at least in part, with the absorption spectrum such that the temperature of the target area of the thermal-sensitive tape 251 is based, at least in part, on an intensity or power of the first spectrum output by the light source 209 when the light source 209 is illuminating the target area of the thermal-sensitive tape 251. Accordingly, (see, supra, FIG. 1B) tack strength or adhesive strength of the thermal-sensitive tape at the target area is based on the temperature of the target area.

It is appreciated that the components of apparatus 201 and thermal-sensitive tape 251 illustrated in FIG. 2 should not be deemed limiting and do not necessarily connote a physical position or organization with respect to one another. Further still, it is appreciated that embodiments of the disclosure may include any number of the components of system 200 and that in some embodiments, one or more of the illustrated components of FIG. 2 may be omitted. For example, in some embodiments apparatus 201 may not include speaker 215, tactile feedback unit 217, optical slider 229, any other component illustrated in FIG. 2, or combinations thereof. Similarly, in some embodiments, thermal-sensitive tape 251 may not include coupling layer 255. Additionally, it is noted that apparatus 201 and thermal-sensitive tape 251 may include additional, unillustrated components described either in the various embodiments of the disclosure or known by one or ordinary skill in the art.

Figure 3A:
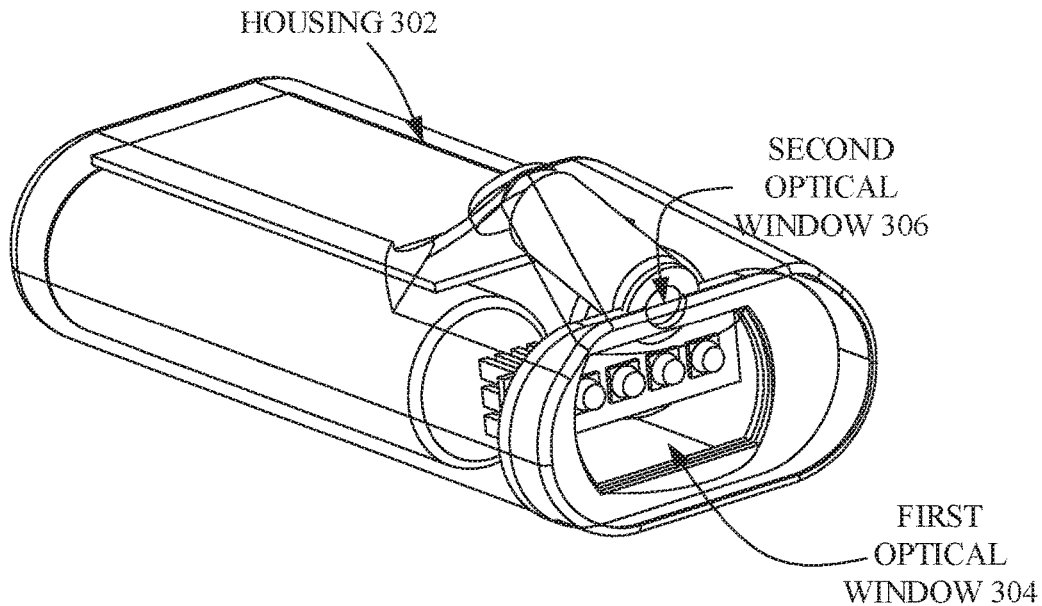
FIG. 3A, FIG. 3B, and FIG. 3C illustrate example perspective views of a handheld optical apparatus for activating a low-adhesion state of thermal-sensitive tape, in accordance with embodiments of the disclosure.
Figure 3B:
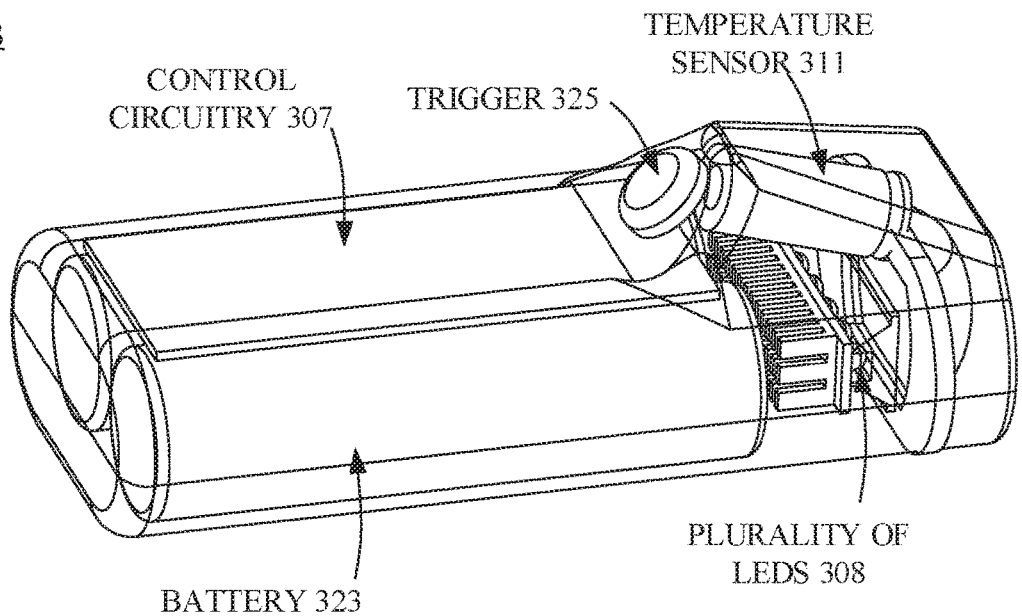
Figure 3C:
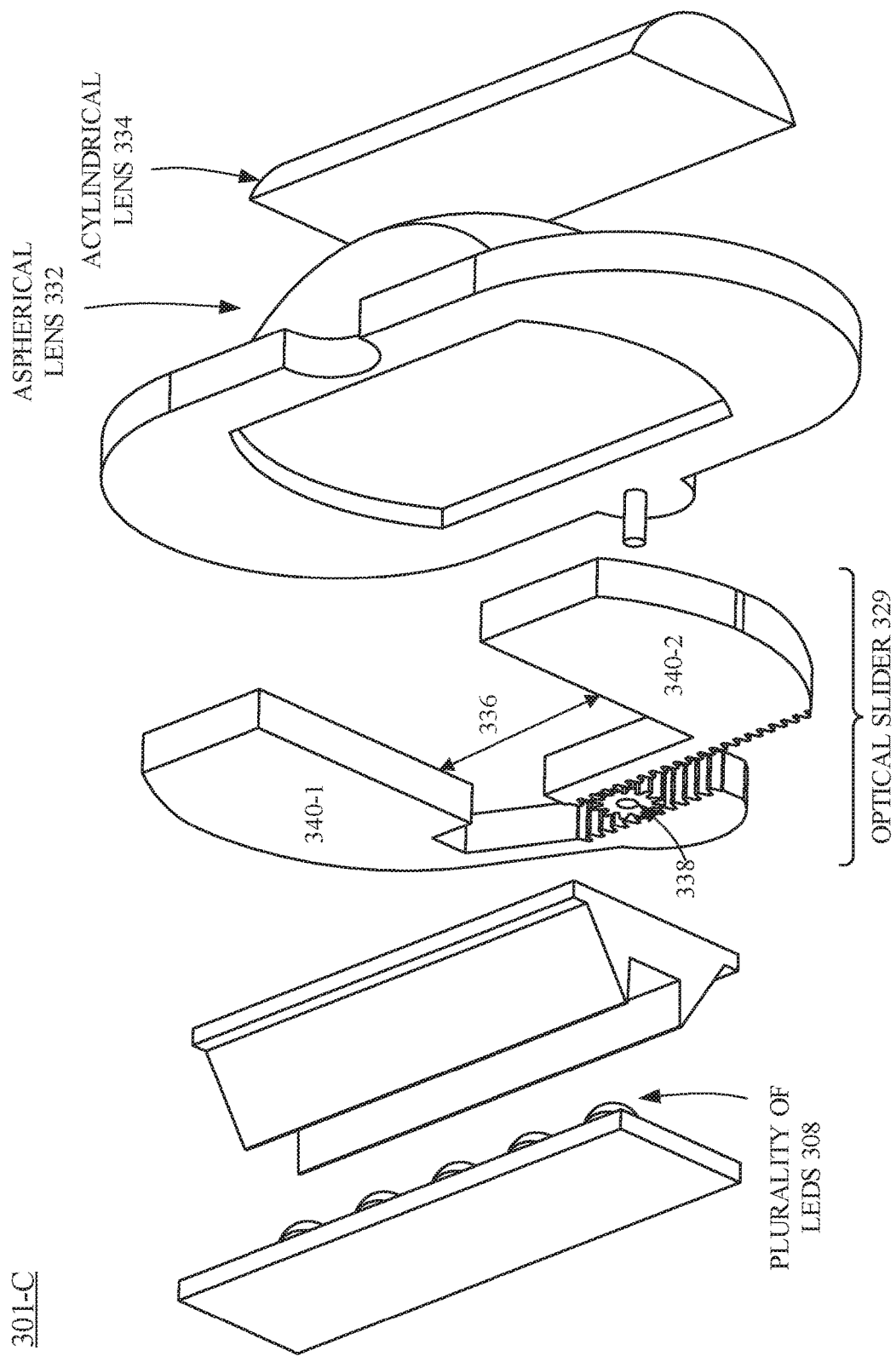

FIG. 3A, FIG. 3B, and FIG. 3C illustrate example perspective views of a handheld optical apparatus 301 for activating a low-adhesion state of thermal-sensitive tape, in accordance with embodiments of the disclosure. Handheld optical apparatus 301 is one possible implementation of apparatus 201 illustrated in FIG. 2 and handheld optical wand 101 illustrated in FIG. 1A. As illustrated in FIGS. 3A and 3B, handheld optical apparatus 301 includes a housing 302, a first optical window 304, a second optical window 306, control circuitry 307, a plurality of light emitting diodes (LEDs) 308, a temperature sensor 311, and batteries 323 (e.g., rechargeable lithium-ion batteries). It is appreciated that the plurality of LEDs 308 may be configured to collectively form a light source and an indicator light with properties similar to those described in relation to liked-named elements of apparatus 201 illustrated in FIG. 2. It is noted that the first optical window 304 and second optical window 306 may have different transmissive properties to enable an optical pathway between the apparatus 301 and a target (e.g., thermal-sensitive medical tape). For example, second optical window 306 may allow for transmission of the second spectrum of electromagnetic radiation (e.g., light with a wavelength between 3 µm and 15 µm) that the first optical window 304 may absorb, reflect, or otherwise attenuate. Similarly, the first optical window 304 may allow for transmission of a first and third spectrum of electromagnetic radiation (e.g., between 750 nm and 1750 nm and between 400 nm and 700 nm, respectively) that the second optical window 306 may absorb, reflect, or otherwise attenuate.

FIG. 3C illustrates an explode view of an embodiment of handheld optical apparatus 301 that further includes optical slider 329, aspherical lens 332, and acylindrical lens 334. As illustrated, optical slider 329 provides a mechanism (e.g., a rotatable gear 338 configured to adjust a position of one or more light shields 340) for adjusting the output path of the plurality of LEDs 308. For example, the opening formed 336 formed by optical slider 329 may be adjusted to provide a narrower or wider opening, which in turn adjusts the width of light output from apparatus 301. As illustrated, the optical slider 329 is disposed between the plurality of LEDs 308 and aspherical lens 332. Similarly, aspherical lens 332 is disposed between the optical slider 329 and the acylindrical lens 334. It is appreciated in some embodiments additional or different optical elements may also be used to shape the output beam of apparatus 301 as targeted.

FIGS. 3D-3G illustrate various non-limiting example arrangements of a plurality of light emitting diodes and temperature sensor, in accordance with an embodiment of the disclosure. The configurations illustrated by FIGS. 3D-3G may be implemented (individually or in combination) in apparatus 301 of FIGS. 3A-3C, apparatus 201 of FIG. 2, and apparatus 101 of FIG. 1A. More specifically, the plurality of light emitting diodes 308 are denoted as "VIS" or "NIR" to indicate, in part, the emissive properties of the given LED 308. For example, 308-NIR corresponds to an LED capable of emitting light of a first spectrum that is outside of the visible spectrum (e.g., between 750 nm and 1750 nm, including a first wavelength corresponding to 940 nm or any or wavelength within the 750 nm to 1750 nm range). Similarly, 308-VIS corresponds to an LED capable of emitting light of a third spectrum that is within the visible spectrum (e.g., between approximately 400 nm and 700 nm, including a third wavelength corresponding to red, blue, green, yellow, or any other color within the visible spectrum). It is further appreciated that each of the temperature sensors 311 is configured to detect a spectrum of electromagnetic radiation (e.g., between 3 μm and 15 μm including a second wavelength corresponding to any wavelength between the frequency range of 3 μm and 15 μm).

In the illustrated embodiment of FIG. 3D, the visible LEDs (308-VIS) are arranged to laterally surround the NIR LEDs (308-NIR) such that when the plurality of LEDs 308 are illuminating the target area of a thermal-sensitive medical tape the NIR LEDs provide heating to the target area while the visible LEDs provide a visual indication of the location (e.g., outline and/or overlap) of the heating.

In some embodiments, the plurality of temperature sensors 311, which in combination with the plurality of LEDs 308, may be used to variably illuminate, heat, and measure temperature information of different zones of the target area. For example, the three different temperature sensors 311 illustrated in FIG. 3C and FIG. 3D are arranged to determine temperature of a first zone, a second zone, and a third zone (e.g., left, middle, and right). Individual NIR LEDs (308-NIR, which may be collectively referred to as a plurality of first LEDs) may be configured (e.g., power or intensity adjusted) such that the individual zones of the target area may be independently controlled in terms of illumination and heating. In some embodiments, the NIR LEDs 308-NIR may be continuously adjusted to provide uniform heating of the different zones based on the temperature information obtained from the temperature sensors 311. This may be particularly useful in situations where the thermal-sensitive tape is affixed to a non-uniform or curved object.

In some embodiments (e.g., as illustrated in FIG. 3D, FIG. 3E, and FIG. 3F) the plurality of visible LEDS (308-VIS, which may be collectively referred to as a plurality of second LEDs) are arranged proximate to the plurality of first LEDs (e.g., 308-NIR) to visually define at least a perimeter boundary of the plurality of first LEDs when the plurality of LEDS 308 (e.g., 308-NIR and 308-VIS) are simultaneously illuminating the target area. This may be achieved by having the plurality of second LEDs (308-VIS) laterally surround the plurality of second LEDS (308-NIR) as illustrated in FIG. 3C, the plurality of first LEDs (308-NIR) arranged as a linear array interspersed with the plurality of second LEDS (308-VIS) as illustrated in FIG. 3E, the plurality of second LEDs (308-VIS-C1 and 308-VIS-C2) longitudinally surround the plurality of first LEDs (308-NIR) as illustrated in FIG. 3F, and/or combinations thereof. LEDs In some embodiments, one or more of LEDs included in the plurality of second LEDs (308-VIS) may be multi-color LEDs (e.g., RGB LEDs) capable of emitting at least a first color C1 and a second color C2. In other embodiments, one or more of the LEDs included in the plurality of second LEDs (308-VIS) may be single color LEDs (e.g., red, green, blue, orange, yellow, etc.) with a first portion capable of emitting the first color C1 and a second portion capable of emitting the second color C2, which is different from the first color C1. In one or more embodiments the different colored visible LEDs (e.g., 308-VIS-C1 and 308-VIS-C2 as illustrated in FIG. 3F) are arranged offset from one another such that when the plurality of LEDs 308 are a predetermined distance from a target area, then the illumination of the different colors overlap one another (e.g., the first color C1 corresponds to red and the second color C2 corresponds to green and when the plurality of LEDs 308 are a pre-determined distance from the target area the illumination overlaps and becomes yellow) as illustrated in FIG. 3F and FIG. 3G. This embodiment enables an apparatus (e.g., any one of apparatus 101 of FIG. 1A, apparatus 201 of FIG. 2, apparatus 301 of FIG. 3A-3C, and/or combinations thereof) to provide a visual indication of when the apparatus is a target distance from the target area. In some embodiments, the target distance may correspond to a position in which the NIR LEDs (308-NIR) become focused on the target area of the thermal-sensitive tape (e.g., to improve heating efficiency by the NIR leads). In the same or other embodiments, one or more of the plurality of LEDs 308 (e.g., such as 308-VIS-C1 and/or 308-VIS-C2 of FIG. 3F and FIG. 3G) may be laser LEDs to improve clarity of when (or when not) the apparatus is at the target distance. It is appreciated that the offset of the different colored LEDs 308 (308-VIS-C1 and/or 308-VIS-C2) shown in FIG. 3F and FIG. 3G may be accomplished in a variety of ways such as adjusting an angle of the LED itself (as shown), including one or more optical elements such as lenses to direct light to a particular position, or combinations thereof.

FIG. 4 illustrates a chart 400 showing relative position in terms of wavelength for a first spectrum of electromagnetic radiation 414, a second spectrum of electromagnetic radiation 416, a third spectrum of electromagnetic radiation 418, a visible spectrum 422, and a first absorption spectrum range 420, in accordance with embodiments of the disclosure. It is appreciated that chart 400 is a non-limiting example and may be utilized to describe features of various components illustrated in FIGS. 1A-FIG. 3G. For example, the output of light source 209 and indicator light 213 of apparatus 201 illustrated in FIG. 2 may respectively correspond to the first spectrum 414 and the third spectrum 418 of FIG. 4. Similarly, the detection or sensing range of the temperature sensor 211 of FIG. 2 may correspond to the second spectrum 416 of FIG. 4. It is further noted in some embodiments, the first absorption spectrum range 420 may be representative of the absorption range of the photosensitive absorbers 259 of the thermal-sensitive tape 251 of FIG. 2.

Referring back to FIG. 4, the first spectrum 414, the second spectrum 416, and the third spectrum 418 are all non-overlapping spectrums (with respect to at least the range defined by the full width at half maximum). Advantageously, this enables enhanced accuracy in terms of heating (provided by the first spectrum 414) without interference from the visual indication of heating (provided by the third spectrum 418). Similarly, temperature sensing accuracy (provided by the second spectrum 416) is enhanced as the first spectrum 414 and the third spectrum 414 do not interface with (e.g., substantially differ from) the second spectrum 416.

Figure 5:
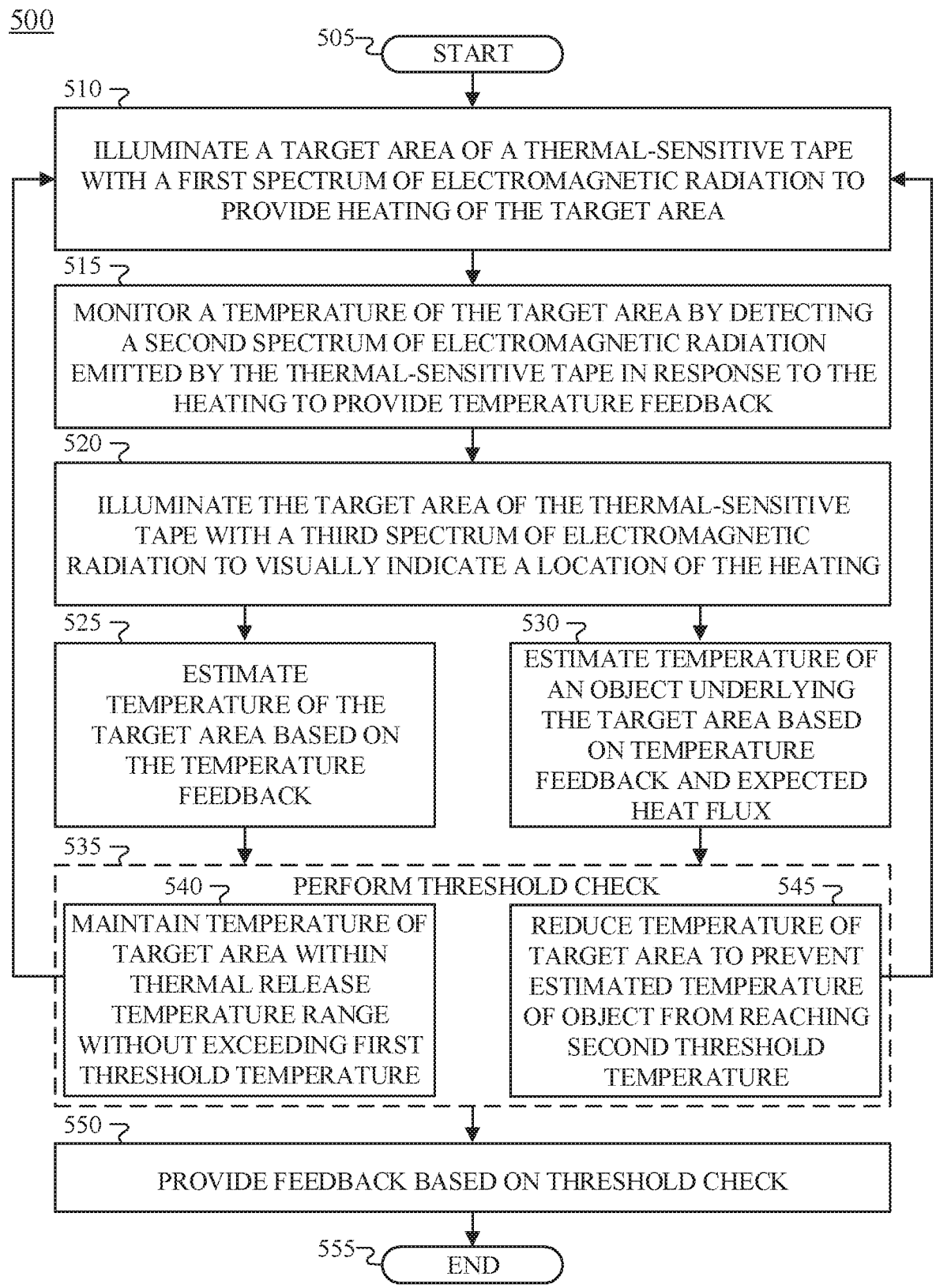
FIG. 5 illustrates a flowchart, which demonstrates a process or method for activating a low-adhesion state of a thermal-sensitive tape without temperature overshoot, in accordance with embodiments of the disclosure.

FIG. 5 illustrates a flowchart 500, which demonstrates a process or method for activating a low-adhesion state of a thermal-sensitive tape without temperature overshoot, in accordance with embodiments of the disclosure. Flowchart 500 may be implemented by various embodiments of the disclosure, including, but not limited to, system 100 of FIG. 1A, system 200 of FIG. 2, and apparatus 301 of FIG. 3A-3C. Referring back to FIG. 5, the order in which some or all of the process blocks that appear in flowchart 500 should not be deemed limiting. Rather, one or ordinary skill in art having the benefit of the present disclosure will understand that some of the process blocks may be executed in a variety of orders not illustrated, or even in parallel. Furthermore, several of the process blocks depict steps that are optional and may be omitted.

Block 505 shows initialization of flow chart 500 for activating a low-adhesion state of a thermal-sensitive tape upon receipt of an initialization signal. In some embodiments the initialization signal may be generated in response to a trigger (e.g., trigger 225 of FIG. 2) being depressed.

Block 510 illustrates illuminating a target area of a thermal-sensitive tape with a first spectrum of electromagnetic radiation (e.g., via light source 209 illustrated in FIG. 2) to provide heating of the target area of the thermal-sensitive tape to within a thermal release temperature range (e.g., as shown in FIG. 1B and corresponding to a temperature greater than T1 or T2). The first spectrum including a first wavelength outside of a visible spectrum.

Block 515 shows monitoring a temperature of the target area by detecting a second spectrum of electromagnetic radiation (e.g., via temperature sensor 211 illustrated in FIG. 2) emitted by the target area of the thermal-sensitive tape to provide temperature feedback.

Block 520 illustrates illuminating the target area of the thermal-sensitive tape with a third spectrum of electromagnetic radiation (e.g., via indicator light 213 illustrated in FIG. 2) to visually indicate a location of the heating. The first spectrum within or otherwise overlapping, at least in part, with the visible spectrum.

Block 525 shows estimating the temperature of the target area based on the temperature feedback. In other words, sensor data from one or more temperature sensors may be obtained, modified or otherwise converted to be indicative of the temperature of the target area at an instantaneous point in time.

Figure 13A:
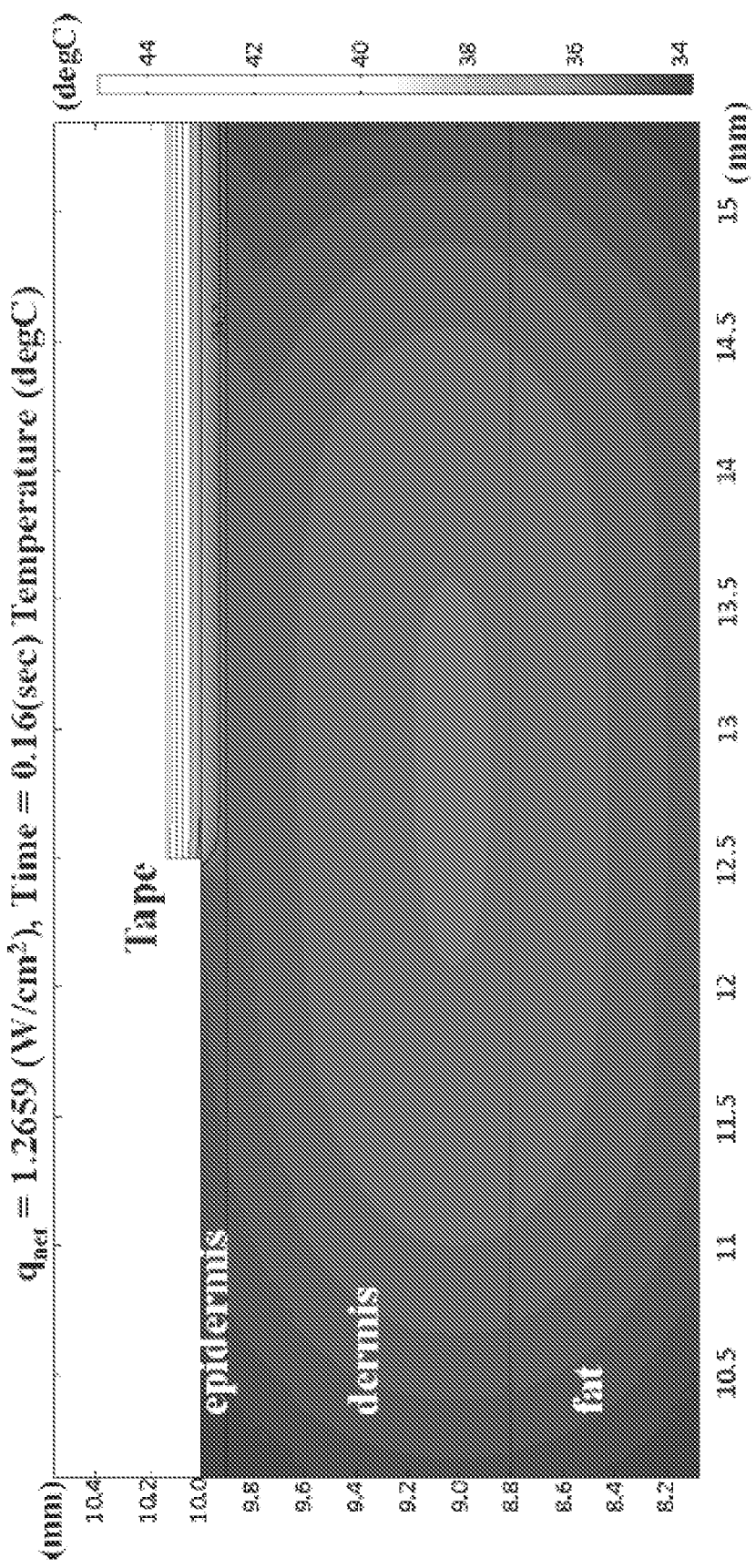
FIG. 13A and FIG. 13B illustrates a simulation result of a skin-UnTape model (RTemp at 45° C. and NIR absorption of 0.855), in accordance with an embodiment of the disclosure.
Figure 13B:
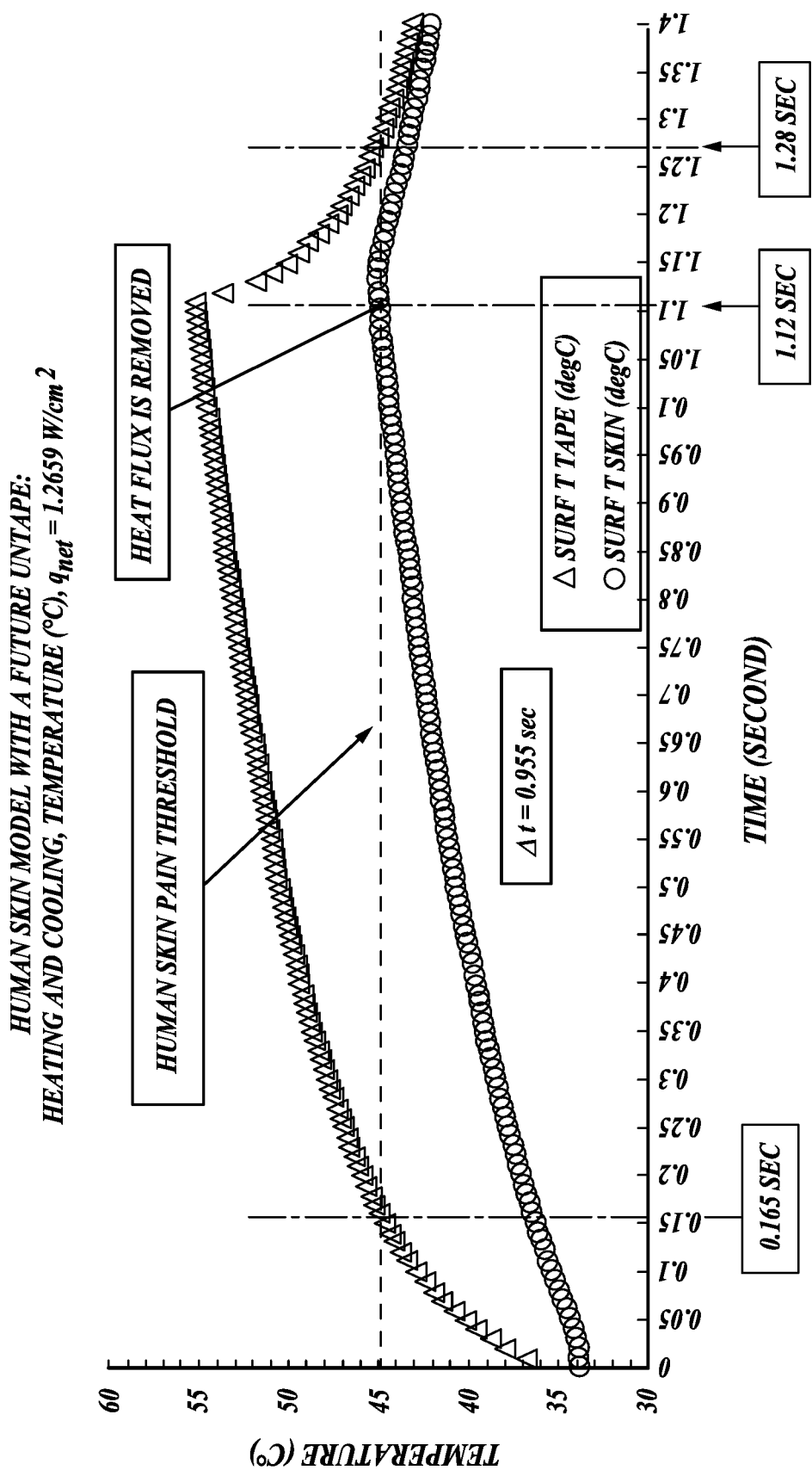

Block 530 illustrates estimating a temperature of an object (e.g., skin) underlying the target area of the thermal-sensitive tape based on the temperature feedback and an expected heat flux (see, infra, FIG. 13A and FIG. 13B). This optional step may be utilized in situations when the temperature of the underlying object the thermal-sensitive tape is adhered to is substantially different or delayed (e.g., in terms of heating) than the temperature of the target area of the thermal-sensitive tape itself. This may occur, for example, in embodiments where photoabsorbers are disposed in a backing layer of the thermal-sensitive tape and not in the thermal-sensitive adhesive itself. However, in other embodiments determining the temperature of the underlying object may not be necessary if there is not a substantial difference between the temperature of the thermal-sensitive tape and the underlying object.

Block 535 shows performing a threshold check based on the estimated temperature of the target area and optionally the temperature of the object underlying the target area.

Block 540 illustrates maintaining the temperature of the target area within the thermal release temperature range without exceeding a first threshold temperature. The first threshold temperature may be, for example, an upper limit beyond which damage occurs to either the thermal-sensitive tape itself and/or the underlying object. In some embodiments, the first threshold temperature may correspond to a threshold of pain that is user configurable (e.g., low, medium, or high). In some embodiments block 540 may proceed to block 510 as the temperature of the target area may be maintained within the thermal release temperature range by adjusting an intensity or power of the first spectrum (e.g., via pulse width modulation) based on the temperature feedback.

Block 545 shows reducing the temperature of the target area to prevent the estimated temperature of the object from reaching a second threshold temperature, which may be prioritized over the first threshold temperature in situations where the temperature of the target area differs substantially from the temperature of the object underlying the target area of the thermal-sensitive tape. As the estimated temperature of the object approaches the second threshold temperature the temperature of the thermal-sensitive tape may be reduced (e.g., by reducing intensity, power, or area of the first spectrum). In some embodiments, the temperature of the object may be reduced by stopping the illumination of the first spectrum.

Block 550 illustrates providing feedback based on the threshold check. For example, the illumination of visible light provided by block 520 may be altered depending on the information determined during the feedback check. In some embodiments, this may include illuminating the target area with a first color of the third spectrum when the temperature of the target area is less than a thermal release temperature range. In the same embodiment, the target area may be illuminated with a second color of the third spectrum when the temperature of the target area is within the thermal release temperature range to provide feedback that the thermal-sensitive tape proximate to the target area is in a low adhesion state. In the same or other embodiments, the feedback may correspond to at least one of visual feedback, tactile feedback, or audible feedback to a user of the apparatus to indicate that the temperature of the target area is within the thermal release temperature range.

Block 555 shows terminating process 500 upon receiving a terminate signal (e.g., releasing the trigger). However, it is appreciated that process blocks 510 through 550 may continue so long as the trigger is held so that a control loop is effectively formed that continually updates the illumination and heating parameters based on the temperature feedback.

A detailed example embodiment of a system. The example embodiment includes experimental results from design and fabrication of components of the system and is not meant to limit any individual aspect of the system or overall system.

As discussed previously, there is a need for high adhesion pressure sensitive tapes that can transition to a lower adhesion at the time of removal. Reported mechanisms to achieve this quick-release range from a multilayer adhesive/antiadhesive transition layer, adhesives with thermally activated components that exhibit phase transitions, and light-sensitive components. Temperature variation by light absorption (photothermal release) offers the opportunity for localized activation using moderate optical power sources. Light absorption additives applied to the backing or adhesive layer can enable the transfer of energy from the light source to the adhesive for temperature switching. The commercial availability of efficient near-infrared (NIR) light-emitting-diodes (LEDs) enables the design of an adhesive removal device with desirable features such as visible light transparency and chemical-free release. This novel approach to activating a thermally switched adhesive may lead to a clinically relevant system that allows painless skin release without the harmful MARSI side effects.

Detailed Example Embodiment of the System

The example embodiment uses a surrogate system to demonstrate the mechanism of rapid and gentle removal of an NIR photothermal sensitive tape (UnTape) and propose a design of a medical tape system based on experiments and numerical analyses. The overall procedure of this study includes the following steps: (1) experimental verification that an example industrial thermal-release tape can be a medical tape surrogate based on a comparative study of the peel strengths of commercially available products, (2) develop a prototype tape (PT) demonstrating the rapid and noncontact photothermal release by applying an NIR absorbing dye to the outer layer of the thermal-release tape, (3) fabricate an NIR light source device with a temperature control feature, (4) numerically model the adhesive thermal switching using a realistic skin substrate, (5) compare the experimental and modeling results and establish a relationship of energy flow from the electrical input to thermal heating of the PT, and (6) determine example design parameters for a clinical UnTape system.

Methods

Adhesion-Switchable Medical Tape

In some embodiments, the system comprises a photothermal sensitive tape (named UnTape and generally referred to as a thermal-sensitive tape or PT) and an NIR light source (named NIR wand). For the proof-of-concept investigation of the UnTape system, we used (1) thermal-switchable tape with clear backing and (2) NIR-absorbing liquid coating. The commercial adhesive film, used in the electronics industry, offers decreased adhesion when heated, which is marketed as Intelimer® Tape (IT), manufactured by Nitta Corporation (Osaka, Japan) under license from the Landec Corporation (Menlo Park, CA). The adhesion strength of IT is significantly reduced near the switch temperature (STemp) of 50° C. The maximum peel strength decreases from 90% (45° C.) to 10% (55° C.).

To increase the temperature of the IT using NIR light, we applied an NIR dye coating (LD920C, Clearweld®, Gentex Corporation, Carbondale, PA) on the top surface of the IT backing. The NIR dye coating efficiently converts the NIR (940-1100 nm) optical power into thermal energy. Our measurements showed that a thick layer of the NIR dye coating (four strokes of a dye applicator) could reduce the IT light transmission near 900 nm by more than 95%, while retaining transmission in the visible spectrum (FIG. 6. Light transmission in the visible region (400-700 nm) is an advantageous feature of medical tape used to secure intravenous devices to allow for monitoring of proper fluid delivery. The absorption of the NIR light depends on the amount of dye material deposited on the IT backing surface. However, the low viscosity, acetone-based NIR dye coating solution uses a marker pen type dispenser, which hindered the deposition of a uniform coating with a consistent thickness. To combat this, a single batch of PT was fabricated with two strokes of the dye applicator, providing a more uniform dye layer. This was used for experimental testing, which reduced the PT transmission near 900 nm to 46%.

One study reported that the temperature threshold of heat induced pain for human skin is approximately 45° C. based on a study with 106 people who were tested on the radial side of the palm and the top of foot. The skin's pain sensation and thermal damage depend on the contact temperature and the duration of exposure. When the contact temperature was 45° C., the results showed that it took more than 30 min to induce skin injury, indicating that the threshold temperature of skin pain at 45° C. for an NIR exposure time of less than 10 s is a conservative estimate for our analyses. However, due to the lack of a commercial source of a lower STemp adhesive tape, the higher STemp Nitta IT with NIR dye coating on its backing was used as the PT throughout the preliminary in vitro testing.

Peel Strength Measurement

Figure 7:
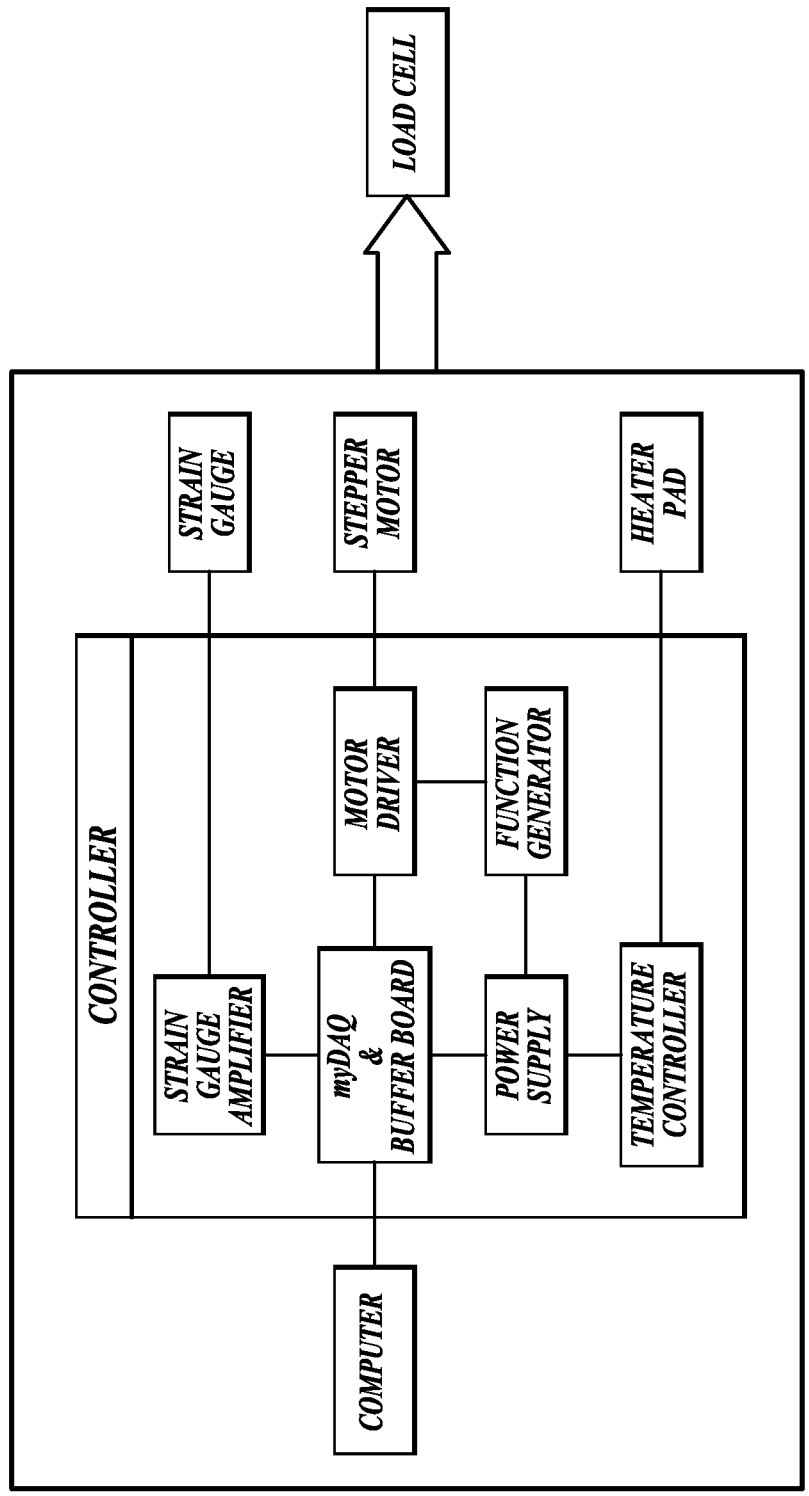
FIG. 7 illustrates an example peel strength test apparatus with the controller box, in accordance with embodiments of the disclosure.

To assess the peel strength of the PT in comparison to other medical pressure-adhesive tapes, we constructed a peel strength test apparatus with a temperature-controlled plate, shown in FIG. 7. The apparatus was designed based on Test Method F of ASTM D 3330/D 3330M. The peel strength test apparatus was framed with aluminum extrusion components and the main components are a linear motion system, a load cell, a heating and temperature sensing platform, and a clamp for holding the tape. The bright annealed 304 stainless steel testing plate is horizontally located under the tape holder, setting an adjustable peeling angle of 90 to 135 deg. The testing has a controllable heating system on the backside. A proportional-integral-derivative (PID) controller and solid-state relay were used to modulate power to the thin film heater. A thermocouple (SA1 Type T, Omega Engineering, Inc., Norwalk, CT) was affixed to the testing plate alongside the tape to monitor the temperature of the adhesion surface.

To measure the peel strength, a tape sample is attached on the testing plate with one end of the tape clamped with the tape holder. The peeling speed is set to 50 mm/min for the peeling distance of 18 mm.

Near-Infrared Light Source

Figure 8:
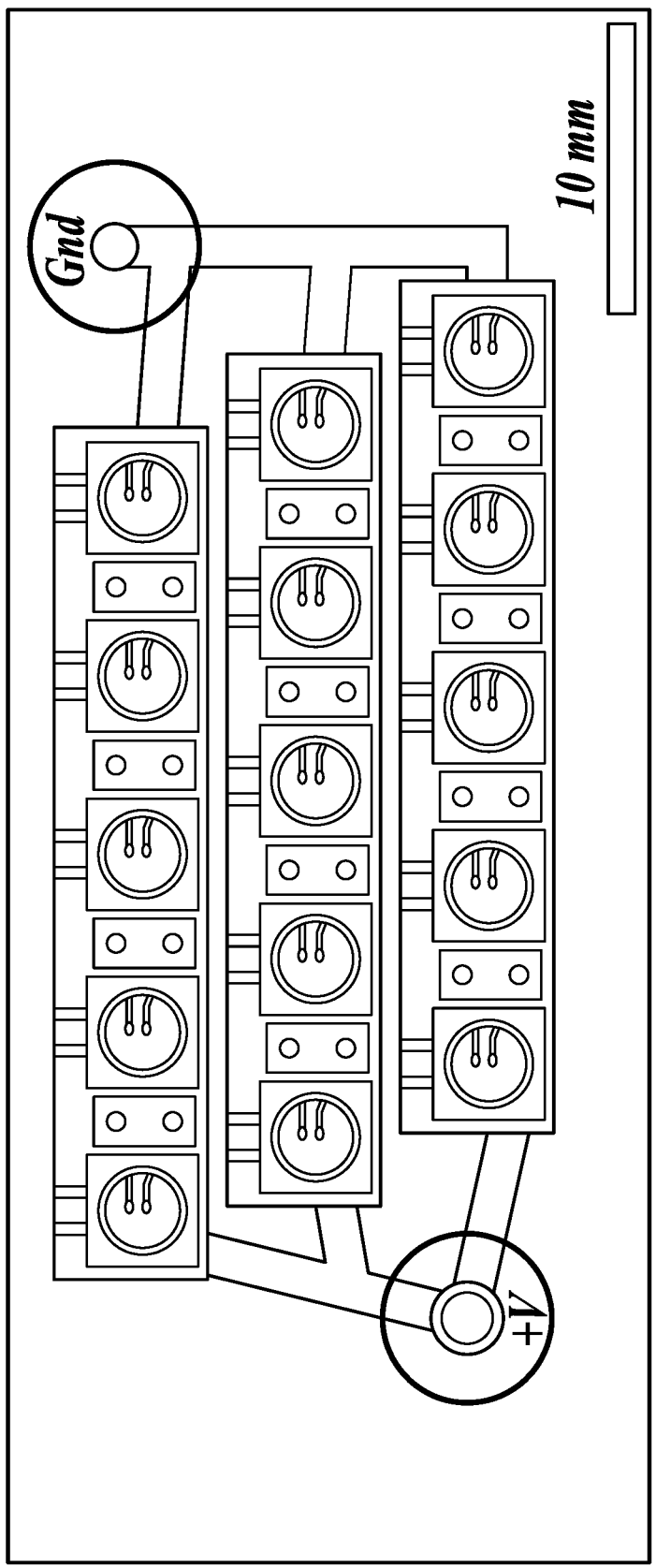
FIG. 8 illustrates an example NIR 15-LED array board with each LED capable of emitting 1450 mW radiometric power at a nominal current of 1.0 A with a forward voltage of 2.9V, in accordance with an embodiment of the disclosure.

The NIR dye coating converts optical energy to heat energy leading to reduced adhesion of the PT. Thus, the adhesive heating mechanism depends on the optical power of the NIR light source, which is a function of the radiometric power, beam angle, and illumination area. To avoid overheating the substrate, the light source needs to sense and monitor the temperature of the PT in real-time. While using the NIR wand on the PT, the temperature is monitored, and when it hits the target temperature (i.e., 55° C.), the user is alerted to initiate the peeling process in order to avoid excess heat application. 15 NIR (940 nm) LEDs (L1I0-0940060000000, Lumileds, San Jose, CA) were used in the prototype NIR light source (shown in FIG. 8), and an infrared (IR) thermometer (MLX90614, Melexis, Concord, NH) was used to monitor the target surface temperature. The LED array of FIG. 8 has three 5-LED rows in parallel, which are positioned 5.5 mm apart and offset 2 mm with another row. The average optical power (measured with 1830-C and 818-IR, Newport, Irvine, CA) at 20 mm is approximately 1.4806 W/cm$^2$.

An Arduino Nano platform was used to manage the custom-made LED driver, IR thermometer, and PID controller. The LED optical power was modulated by the PID controller to maintain the target temperature as sensed by the IR sensor with minimal latency. The prototype NIR light source was later packaged with a three-dimensional printed case.

Heat Transfer Experiments and Finite Element Simulation

Acrylic Substrate as a Test Model

The UnTape photothermal heating mechanism by NIR light exposure was evaluated using an acrylic substrate as a test model for heat transfer analysis. The averaged thermal properties of skin, acrylic (polymethylmethacrylate), and 304 stainless steel are listed in Table 1. Because of the lower conductivity and specific heat of acrylic, the thermal inertia ($I=\sqrt{k\rho c_p}$) of acrylic is approximately one half of the averaged skin thermal inertia. The standard for testing adhesive tapes uses 304 stainless steel as the substrate, which has a thermal inertia 3× higher than skin. This significantly higher thermal inertia of stainless steel prevents temperature increases on the illumination surface. Thus, the 6 mm thick acrylic substrate was used for NIR heating experiments since it has comparable thermal conductivity to skin and also has well-characterized thermal properties that work well with finite element analysis. In addition, the low thermal inertia of acrylic adds additional safety factors in future human skin experiments, because the sensible temperature at the skin surface is expected to be lower than at the acrylic surface.

TABLE 1

Thermal properties of skin, acrylic, and 304 stainless steel.

|  | Skin (epidermis + dermis) | Acrylic | 304 stainless steel |
|---|---|---|---|
| Thermal conductivity, k (W/(m K)) | 0.343 | 0.190 | 160 |
| Density, $\rho$ (kg/m$^3$) | 1200 | 1200 | 7800 |
| Specific heat, $C_p$ (kJ/(kg K)) | 3.44 | 1.47 | 0.480 |
| Thermal inertia, I (kJ/(m$^2$ K s$^{1/2}$)) | 37.6 | 18.1 | 244.8 |

Near-Infrared Heating Experiments

To examine the performance of the NIR LED arrays and proposed operating specifications, experimental temperature measurements were conducted with the acrylic substrate and PT. For each LED, a constant-current driver supplied three different input currents of 500.0, 666.7, and 833.3 mA, and the corresponding forward voltages of 2.67, 2.78, and 2.83 V, respectively. The threshold temperature in the PID controller was set to 55° C., which is the release temperature (RTemp) of the PT. When the temperature reading reached the threshold, the pulse width modulation output from the microcontroller modulated the light intensity to maintain a constant temperature at this threshold value.

COMSOL Simulations

The numerical modeling was performed to establish the correlation of energy conversion between the experimental measurements and the simulation. After the correlation is established, the future photothermal sensitive tape with a lower adhesion STemp of 40° C. and a higher NIR absorption can be designed based on the numerical model.

Figure 9A:
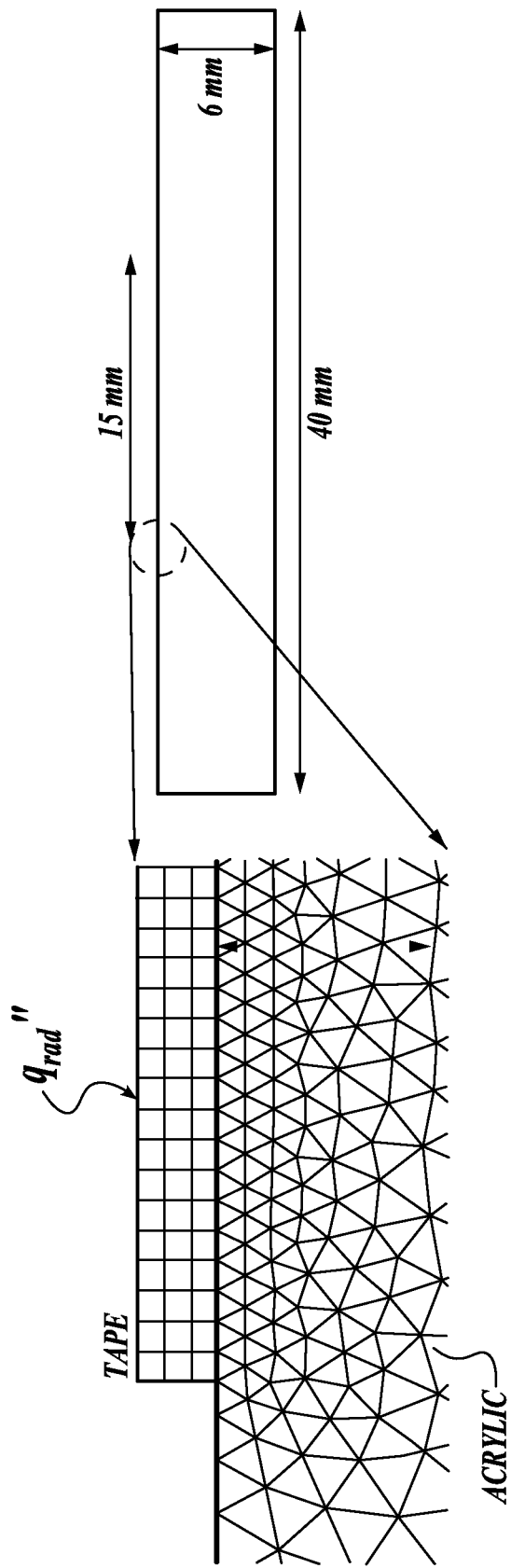
FIG. 9A and FIG. 9B illustrates example geometry and local meshing grid of a PT-acrylic model and UnTape-skin model, in accordance with an embodiment of the disclosure.
Figure 9B:
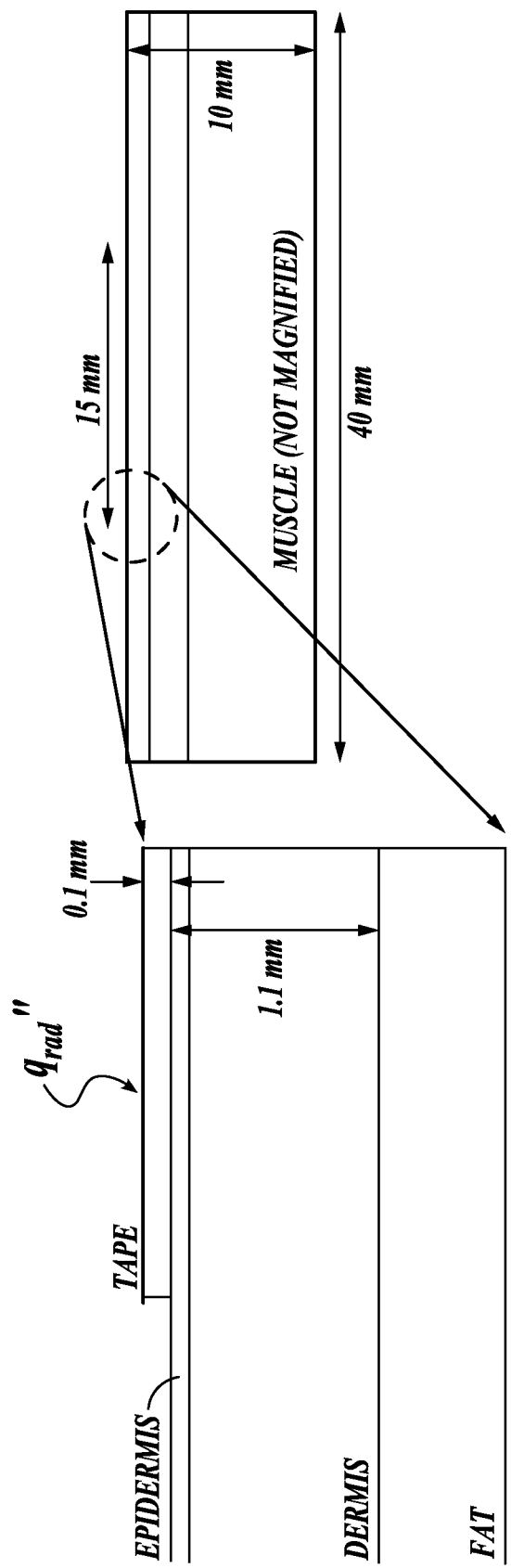

The finite element method simulations using COMSOL MULTIPHYSICS Version 5.4 platform were conducted to analyze the NIR heating experimental results and to adjust the performance of the NIR LED board and control system for human skin. FIG. 9A and FIG. 9B illustrates an example geometry and local meshing grid of a) PT-acrylic model and UnTape-skin model, in accordance with an embodiment of the disclosure. The upper surface of the tapes receives the heat flux. Both tapes are modeled as a single material (PET) for simplicity; thus, an adhesive layer and an NIR dye coating layer were not included. The properties of the layers are presented in Table 2. FIG. 9A shows the geometry and mesh of the PT and acrylic substrate model. The thermophysical properties of the materials are included in Table 2. A two-dimensional time-dependent study was performed for 5 s for the parameter sweep of grad, the radiative heat flux on the surface of the PT, between 0.3 and 1.0 W/cm$^2$. This heat flux was equivalent to the net NIR exposure converted to heat energy after subtracting the reflection and transmittance of NIR from the PT. Meshing consists of a linearly mapped mesh for the PT domain and a triangular mesh for the acrylic domain. All surfaces were set to a diffusive surface to adjust to the room temperature, 22° C.

TABLE 2

Thermophysical properties of the components in the COMSOL models: PET, acrylic, epidermis, dermis, fat, and muscle (human skin properties are from Okabe et al.).

|  |  |  | PET | Acrylic | Epidermis | Dermis | Fat | Muscle |
|---|---|---|---|---|---|---|---|---|
| Thickness | d | mm | 0.13 | 6 | 0.1 | 1.1 | 2 | 6.8 |
| Thermal conductivity | k | W/(m K) | 0.155 | 0.19 | 0.235 | 0.445 | 0.185 | 0.51 |
| Density | p | kg/m$^3$ | 1390 | 1200 | 1200 | 1200 | 1085 | 1030 |
| Heat Capacity | $C_p$ | kJ/(kg K) | 1.17 | 1.47 | 3.59 | 3.30 | 2.67 | 3.80 |

Based on the experimental temperature data and corresponding numerical analysis from the acrylic substrate testing, an additional simulation with a human skin model was studied where the RTemp of the PT was set to 45° C., our conservative threshold temperature of human skin pain. The geometry, mesh, and thermal properties of human skin are shown in FIG. 9B and Table 2, and the initial temperatures of the epidermis, dermis, and fat were set to 34° C. and 35° C. for the muscle layer. In the skin model simulation, we considered a photothermal sensitive tape (UnTape) of which the RTemp is 45° C. and the NIR absorption is 0.855. The NIR absorption of UnTape was estimated from the reflectance of 0.1 and the multilayer NIR dye coating absorption of 0.95 (shown in FIG. 6 from the multilayer NIR dye coated PT). The effective heat flux calculated from the incident NIR optical intensity and the NIR absorption of the UnTape was directly applied to the simulation.

Results

Peel Strength Measurement Using Acrylic Substrate

Figure 10:
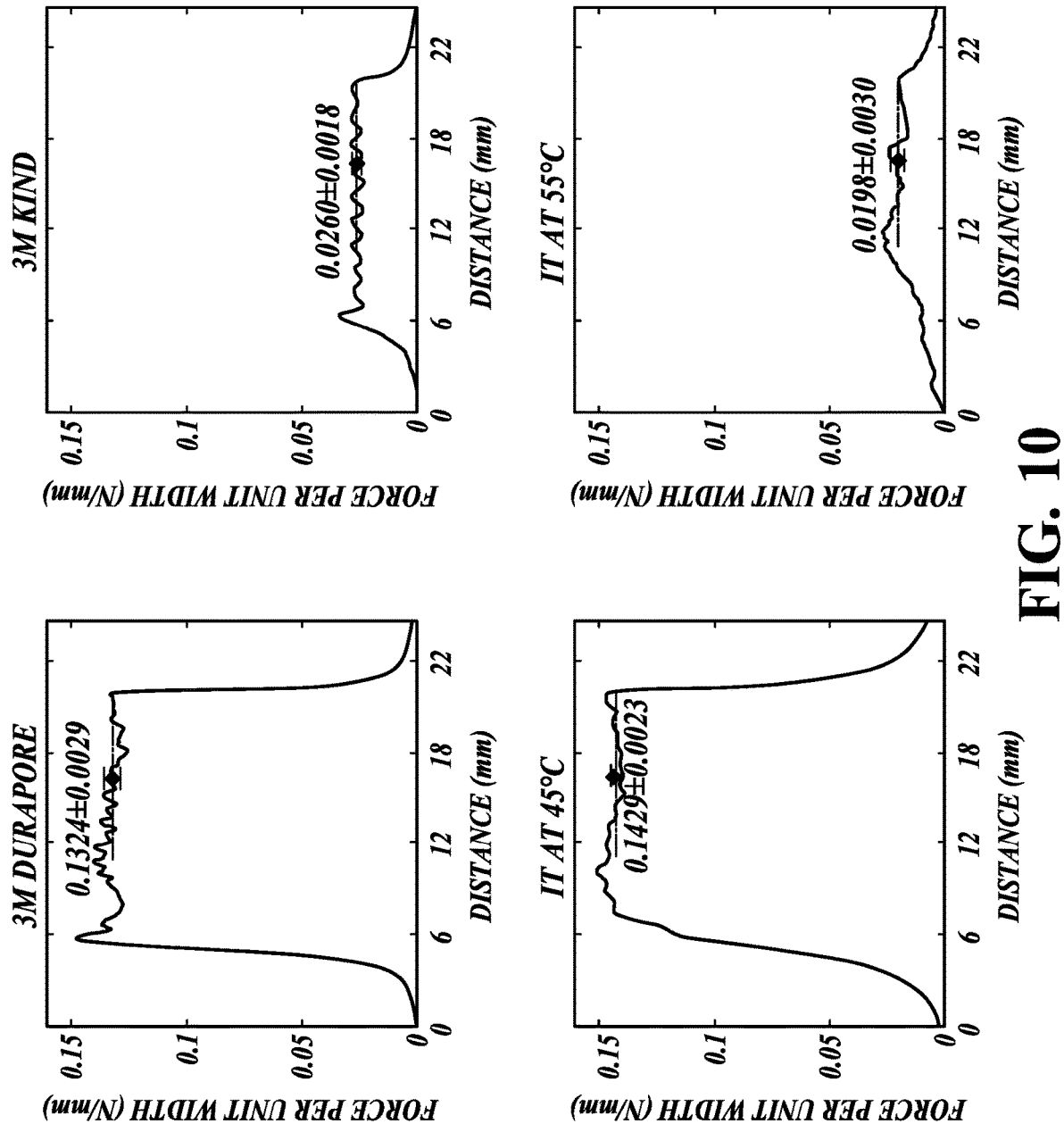
FIG. 10 illustrates example peel strength comparison, in accordance with embodiments of the disclosure.

FIG. 10 illustrates example peel strength comparison, in accordance with embodiments of the disclosure. Peel strength comparison: 3M Durapore, 3M Kind, and IT at 45° C. and 55° C. The IT has a STemp at 50° C. and shows the adhesion force drop by an average of 86% between 45° C. and 55° C. The adhesion force of the IT at 45° C. is stronger than 3M Durapore but also becomes as low as 3M Kind at 55° C. The bars and marks represent the average and standard deviation of the peel strength between 12 and 20 mm in the peeling distance. 3M Durapore™ surgical tape and 3M Kind removal silicon tape were chosen to represent the highest and lowest adhesive forces among common medical pressure adhesive tapes. Using the peel strength test apparatus, five measurements at the 90 deg peeling angle were collected for each tape sample attached on the acrylic substrate and were averaged to evaluate the required peel forces per unit width. The comparison clearly shows that the selected commercial surrogate thermal sensitive IT has an adhesion strength equivalent to the 3M Durapore high-tack tape at 45° C. After the temperature increases to 55° C., the adhesion force drops by 86%, which is comparable to the low adhesive strength of the 3M Kind tape.

Near-Infrared Heating Experiments with an Acrylic Substrate

Figure 11:
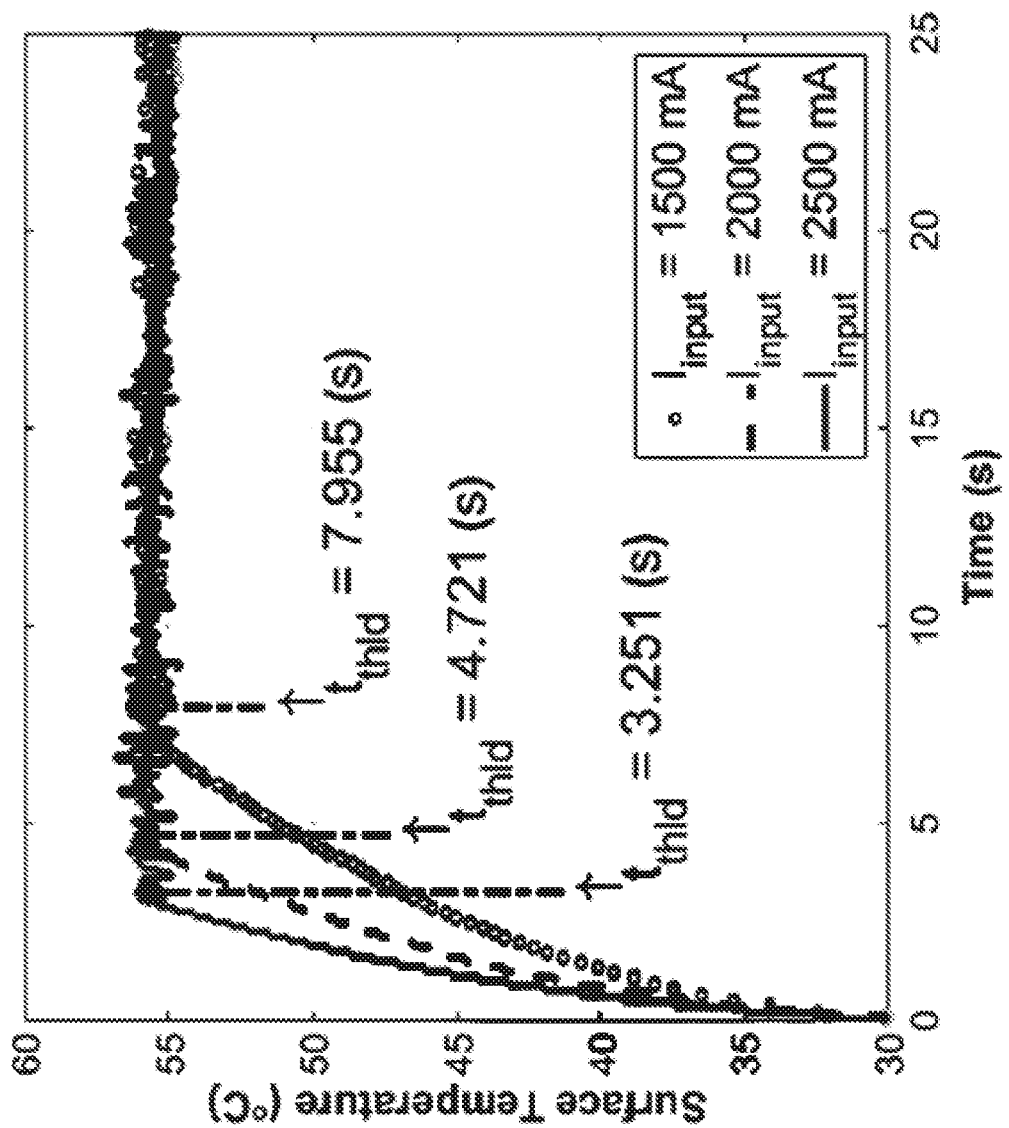
FIG. 11 illustrates transient temperature changes of the PT by NIR exposure, in accordance with embodiments of the disclosure.

FIG. 11 illustrates transient temperature changes of the PT by NIR exposure, in accordance with embodiments of the disclosure. Various currents (1500, 2000, and 2500 mA) were applied to the LED array, and the higher input lead to the shorter times to reach the threshold temperature. The time to threshold temperature was marked with black stars.

After that point, the surface temperatures were maintained by the PID controller. Because the power supply of the prototype NIR wand was set to the current of 2 A, the experimental data fitting with the COMSOL simulation shown in FIG. 12 was based on the NIR heating time of 4.72 s at 2 A. More specifically, FIG. 11 shows the temperature profiles of the PT during the NIR light irradiation. The elapsed times for the threshold temperature, 55° C., at each forward current are shown. The input currents at 1500, 2000, 2500 mA were applied to three 5-LED rows so that each LED was operated at 500, 666.7, and 833.3 mA, respectively. The heating profile and operating conditions at 2000 mA were exploited to estimate the effective optical power of the NIR light source in conjunction with MATLAB and COMSOL simulations.

The emissivity compensation for the IR temperature measurement was not predetermined because of the design flexibility for various surface measurements. Therefore, the emissivity compensation based on the reference emissivity (E=0.94) of polyethylene terephthalate (PET) and the room temperature (Tambient=22° C.) was followed. The corrected temperature of 56.79° C. was obtained by the following equation (1), $$T_{target} = \sqrt[4]{\frac{T_{sensor}4 - (1-\varepsilon) \cdot T_{ambient}4}{\varepsilon}} \quad (1)$$

Comparison of Near-Infrared Optical Power Intensities

Figure 12:
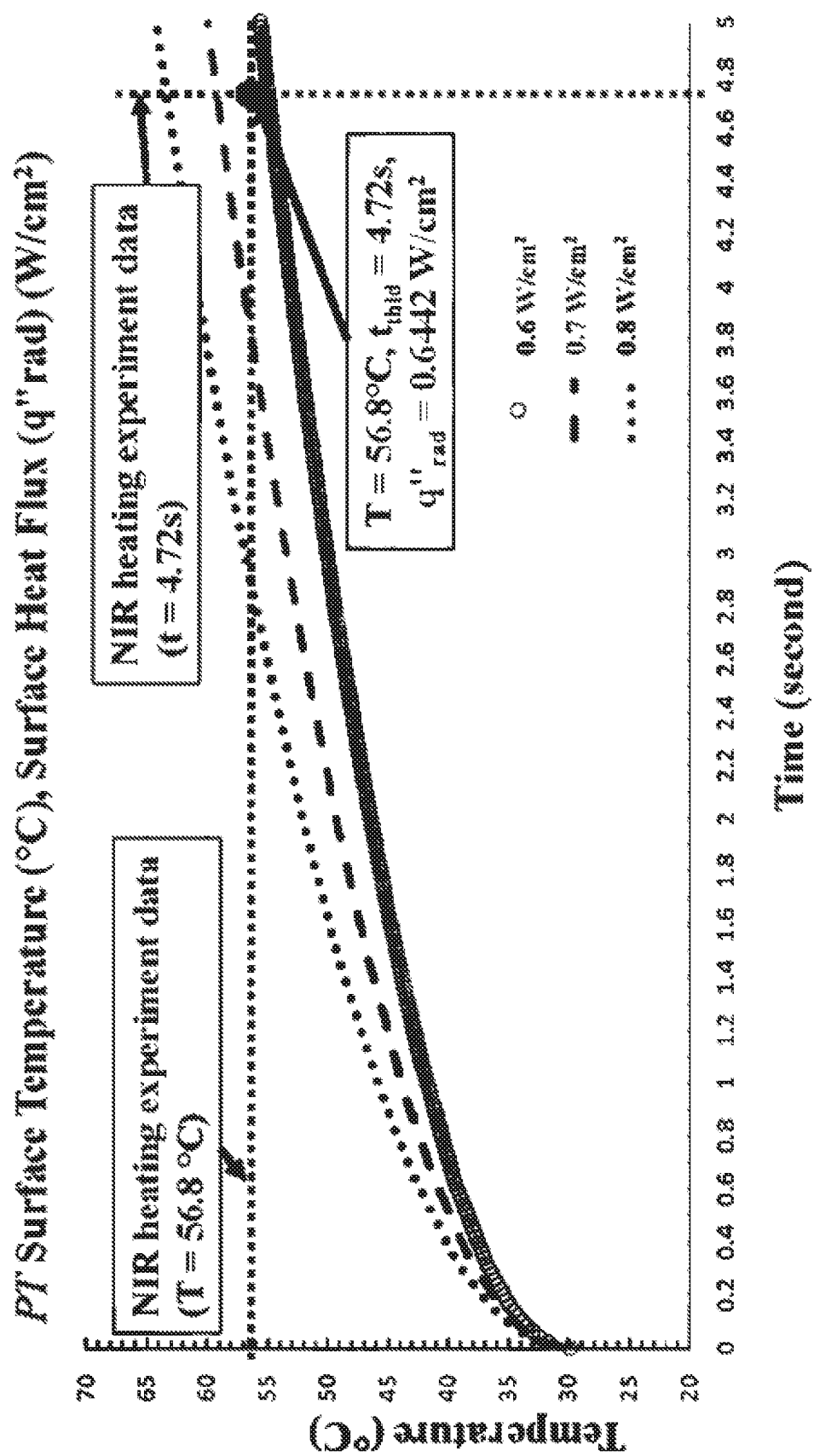
FIG. 12 illustrates COMSOL results from the tape-acrylic model FIG. 9, in accordance with embodiments of the disclosure.

From the COMSOL simulation model, the temperature profiles of the PT with various heat fluxes are plotted in FIG. 12. More specifically, time-dependent temperature increase by the surface heat flux at 0.6, 0.7, and 0.8 W/cm² are plotted in FIG. 12. The threshold temperature and the elapsed time of NIR heating from the NIR heating experiment is overlaid; a round dot is the crossing point between the horizontal dotted line (the threshold temperature at 56.8° C.) and the vertical dotted line (the elapsed time to reach the threshold temperature). The heat flux of 0.6442 W/cm² at the crossing point was interpolated from the COMSOL temperature profiles.

As we have the experimental results of the threshold temperature of the PT surface and the time to reach the threshold temperature, those values are overlaid in the figure: the horizontal dotted line represents the threshold temperature measured from the experiments and the vertical dotted line represents the elapsed time to reach the threshold temperature. The data point of 0.6442 W/cm² in the simulation was interpolated as the best-fit heat flux based on the experimental results. The heat flux applied to the COMSOL model did not include optical power conversion parameters, such as the reflectance and transmittance of the PT. Therefore, the estimated heat flux is the net light energy absorbed by the PT backing.

From the LED specification data, the optical intensity of the LED arrays, I, can be estimated as follows:

$$I_{est} = \frac{n \cdot \Phi_{LED,1A} \cdot \eta_{F.A.} \cdot \eta_{area} \cdot \eta_{temp} \cdot (1 - \gamma - \tau)}{A_{illumination}} \quad (2)$$

where n is the number of LEDs, $\Phi_{LED,1A}$ is the nominal radiometric power at the input current of 1.0 A, $\eta_{F.A.}$ is the proportionality of radiant power at a different input current, $\eta_{area}$ is the radiant power ratio for the effective illumination area, $\eta_{temp}$ is the output variation by the LED case temperature, $\gamma$ is the surface reflectance, $\tau$ is the object transmittance, and $A_{illumination}$ is the area of illumination. From the specification data, the $\Phi_{LED,1A}$ is 1450 mW, and $\eta_{F.A.}$ is linearly proportional to input current (e.g., $\eta_{F.A.}$=0.8 if the input current is 0.8 A). At the illumination distance of 20 mm between the LED board and the PT, $\eta_{area}$ was approximately 0.536 for the window size is 31 mm 16 mm. The reflectance, $\gamma$, and transmittance, $\tau$, at 940 nm were directly measured from the IT and PT, respectively, using the optical power meter (1830-C and 818-IR, Newport, Irvine, CA): $\gamma$=10.5% and $\pi$=46.0% based on the PT that was coated twice with the Clearweld NIR dye. We assume that the reflectance of the PT and the IT are the same, so the net absorption of the PT coating layer, u, can be estimated as follows: $\alpha$=(1-$\gamma$-$\tau$)= 0.435. As predefined in the prototype NIR wand design, $A_{illumination}$ and the window are considered the same size.

The net NIR optical intensity delivered by the NIR LED array was measured by the optical power meter independently from the numerical simulation and the specification calculation.

The COMSOL results were based on the heat energy released on the surface of the PT backing, which assumes that the net NIR optical power was absorbed only by the NIR dye coating. On the other hand, the NIR LED optical power measurement (using the optical power meter) corresponds to the raw radiant flux before hitting the PT. Therefore, in order to juxtapose the optical power measurement (using the optical power meter) with the values from NIR LED optical power calculation (using the LED specification data) and COMSOL results, the measurement from the optical power meter was further corrected by the absorption of the PT.

$$I_{exp} = I_{measured} \cdot \alpha = I_{measured}(1-\gamma-\tau) \quad (3)$$

Thus, the $I_{comsol}$, from the numerical simulations, can be compared with the $I_{est}$, the estimated optical power based on the LED specification sheet, and $I_{exp}$, from the optical meter experiments. Table 3 shows the comparison of the results from three independent calculations and measurements, which were all based on the experimental conditions of a 2 A input current, 4.72 s illumination time, and the 20 mm distance between the LED board and the PT. The radiant flux from the optical power meter measurement can be considered as the actual NIR optical power from the LEDs. All three optical power intensities are within the error range of less than 5%.

TABLE 3

Comparison of the heat or NIR radiant fluxes required to increase the temperature of the PT up to 55° C.

| Method | Estimation from LED specification $I_{est}$ | NIR testing with COMSOL simulation $I_{comsol}$ | Optical power measurement $I_{exp}$ |
|---|---|---|---|
| q" net (W/cm$^2$) | 0.6821 | 0.6442 | 0.6651 |
| Error (%) | +2.5 | −3.2 | N/A |

Note:
$I_{est}$ was estimated from the LED specification data, $I_{comsol}$ was evaluated from the COMSOL of a PT-acrylic model fitting the NIR heating experiment, $I_{exp}$ was measured using the optical power meter and converted to the optical intensity. Iest and Iexp were calibrated by the NIR dye absorption of the PT in order to compare NIR intensity and heat flux absorbed at the NIR dye layer. The error is calculated based on the optical power measurement.

Skin Model Simulation

At this stage of development, the PT and NIR lighting source could be considered unsafe for human subject testing. However, we estimated the required thermal heat flux to reach the RTemp at 55° C. from the NIR light source device based on the simulation and NIR PT in vitro measurements. Thus, the estimated heat flux can be used as an NIR heating simulation for human skin based on the current NIR light source design. The transient heating effect on the skin model to RTemp at 45° C. was considered and the effective heat flux by NIR absorption was set to 1.2659 W/cm$^2$. FIG. 13A, FIG. 13B, and Table 4 summarize the setting parameters and results of the human skin model simulation. As illustrated in FIG. 13A and FIG. 13B, due to the high NIR absorption of the UnTape, the effective heat flux is 1.2659 W/cm$^2$ estimated from the NIR radiant power of the prototype NIR wand and the NIR absorption. FIG. 13A shows the temperature distribution of a human skin model at t=0.16 s. Epidermis, dermis, and fat layers have different properties from top to bottom (the skin properties are presented in Table 2). FIG. 13B shows temperature profiles on the surface of the UnTape and the interface between the UnTape and the skin surfaces. The pain threshold temperature of human skin (horizontal dotted line at 45° C.), and the heating times for the tape surface and skin surface to reach 45° C. are presented; 0.165 s and 1.12 s (vertical dotted lines). Cooling profiles are also shown after the heating is stopped at the human skin pain threshold, t=1.12 s. As the UnTape has a higher NIR absorption than that of the PT, the elapsed time to reach 45° C. at the outer surface was an estimated 0.165 s and 1.12 s for the UnTape tape and skin, respectively. If heating continues to the human skin pain threshold (45° C.), the UnTape surface temperature reaches 55° C., and cooling occurs relatively quickly (<0.2 s). This significant temperature difference (10° C.) across the small thickness of the tape (130 μm) could be reduced in some embodiments, in which the NIR absorbing dye is embedded in the backing, an intermediate coupling layer, or the adhesive layer.

TABLE 4

Simulation settings and the results of the human skin--UnTape model

| | |
|---|---|
| RTemp (° C.) | 45° C. |
| NIR absorption of a tape | 0.855 |
| Incident NIR optical intensity (W/cm$^2$) | 1.4806 |
| Effective heat flux input (W/cm$^2$) (absorbed by the tape) | 1.2659 |
| Elapsed time for RTemp at tape surface (s) | 0.165 |
| Elapsed time for RTemp at skin surface (s) | 1.12 |

Discussion

A coating of a NIR absorbing dye was coated on the outer surface of a thermal-sensitive tape. Our tests demonstrated that using the absorbed optical energy supplied by the NIR LEDs (FIG. 10), the tape adhesion force dropped an average of 86% at the RTemp (55° C.). This has demonstrated that the NIR light source can efficiently increase the tape's bulk and surface temperature to ease removal. Additionally, the industrial thermal-release film tape (IT) successfully acted as a surrogate for comparing medical tape adhesion levels. The peel strength test showed that the PT can have stronger adhesion than high-tack surgical tape (3M Durapore) while exhibiting release properties at the RTemp equivalent to extra gentle silicone-base medical tape (3M Kind). Retaining the PT visible light transparency ensures that the medical staff can view the skin beneath the dressing, allowing the applicator to accurately attach the taped device to the skin and to observe any skin damage or irritation.

In this study, an adhesion RTemp of 55° C. is considered higher than the 45° C. threshold of human skin pain level. The application of the NIR absorbing dye solution on the backing of the IT was done without professional coating techniques, which produced a nonuniform coating layer, possibly leading to irregular NIR absorbing on the PT surface area. Despite this variation, the preliminary measurements with the engineered prototype tape and light source device provided valuable insight for the design of a UnTape system. This system may include a flashlight-like NIR light source and NIR-sensitized medical tape that efficiently switches adhesion at 40° C., allowing for the UnTape to achieve full release at 45° C.

We investigated the prototype NIR light source optical power intensity and heat flux required to heat the PT to RTemp (55° C.), as shown in Table 3. Based on the optical power measurement, the estimated NIR optical power intensities from the LED specification data and the numerical simulation were in agreement to within 5%.

Figure 6:
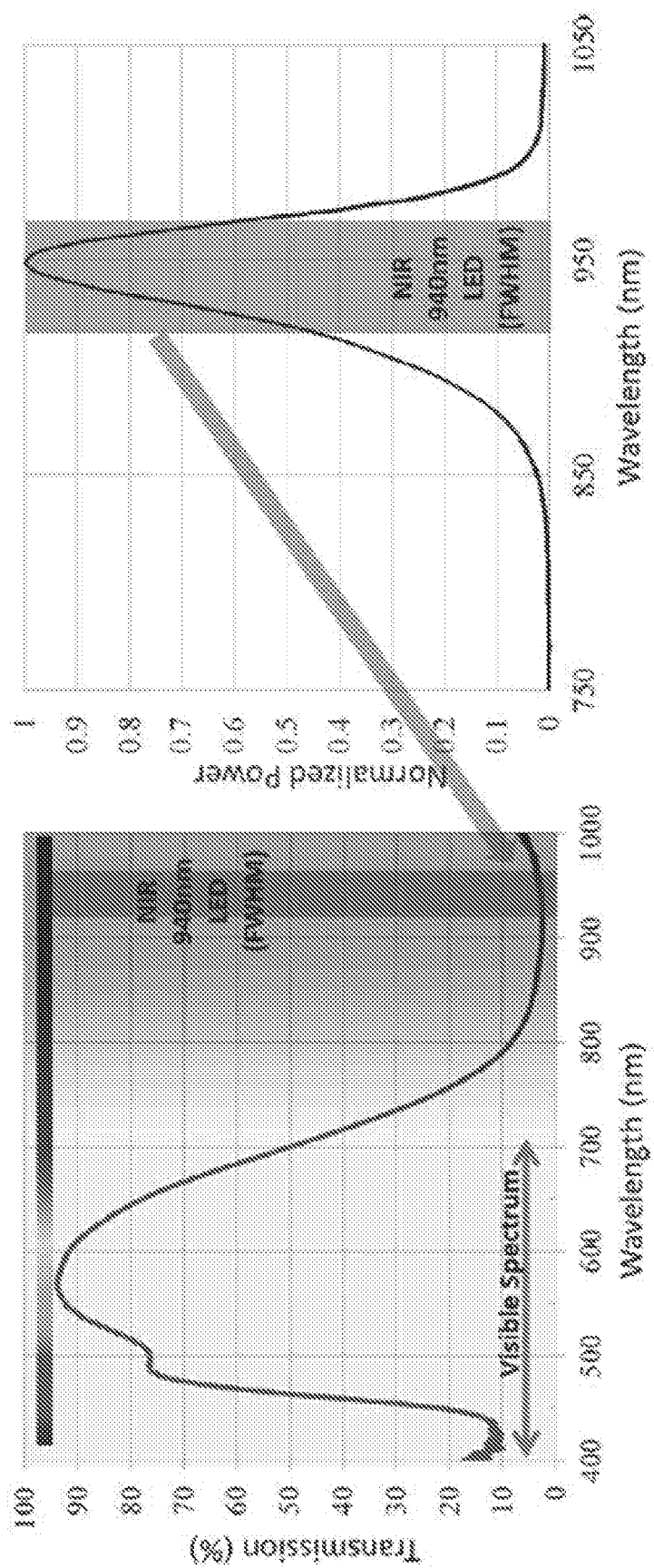
FIG. 6 illustrates an example transmission spectrum of a multilayer NIR dye coating (left) and an example spectral power emission of a Luxeon NIR LED (right), in accordance with embodiments of the disclosure.

The NIR dye absorption depended significantly on the amount of dye coating. The twice coated PT was used to provide consistent NIR dye coating, but the high NIR transmittance of the PT, 46%, was not desirable. Adding more layers of the NIR dye coating only slightly increases absorbance above 95%, with diminishing returns due to surface reflection, as shown in FIG. 6. Although we need more information about the photothermal transduction mechanism, including multiple reflections in a multilayer NIR dye coating structure with various illumination angles on different skin conditions and pigmentation, for this analysis we will assume that the dye layer absorbs 95% of the NIR incident illumination around 940 nm without significant reduction of visible light transparency.

We investigated the temperature change on a human skin model based on the heat flux value and fitting data from the experiments and simulations using the acrylic substrate. Using the NIR light source, it took only 1.12 s to heat UnTape to the human skin pain threshold. The one second NIR exposure for medical tape removal is a promising result for the future UnTape system, which will have an optimized tape design and NIR illumination approach. However, the rapid heating near the skin will require strict temperature control that may extend the heating time to reduce the risk of overheating.

The environmental temperature is also an important variable as it affects tape adhesion. At this stage, we are assuming a controlled environment in hospitals or caregiving facilities. Additional experiments and simulations are needed to understand the stability of the product during transportation and storage at extreme temperatures. Regardless, once applied, the tape temperature is regulated by body temperatures, as the heat conduction rate is significantly higher than the convection rate.

An Example Embodiment

Photothermal Sensitive Tape, UnTape

A photothermal sensitive tape having a low adhesive STemp and RTemp, and a high NIR light absorption, leading to improved heat conversion. The NIR absorbing dye is uniformly distributed in the UnTape adhesion layer. The tape does not exceed the human skin pain threshold. The temperature dependence of the adhesive allows for higher adhesion forces without the difficult removal process. The adhesive layer may be designed in different ways based on the target patient. For example, retention of a peripheral intravenous catheter on the skin provides stabilization and avoids risk of infection. As UnTape may have high adhesion, it can be highly perforated for other medical functions. A highly perforated tape with a hydrophobic backing layer may allow for breathability, elasticity, and water resistance. Perforated UnTape will disperse the heat over the skin surface, minimizing the risk of skin pain.

Near-Infrared Wand

Power consumption is an important consideration for the NIR light source design. Due to the inefficient conversion process from electrical energy to heat energy, the input power for the wand may be as high as 30 W. In some embodiment, the low adhesion state of the UnTape is activated by "hand scanning," in which a user holds the NIR wand by hand and manually sweeps over UnTape. A 18 mm×65 mm rechargeable lithium-ion battery is considered as a power source. This 3000 mAh battery has a nominal voltage of 3.6V and an end-of-discharge voltage of 2.8V. Table 5 presents the power consumption based on the experimental results and numerical simulations. One or two 18650 batteries were considered, and continuous running times of >30 min and >60 are expected, respectively. The battery capacity was conservatively applied at the end-of-discharge voltage. Therefore, incorporating a voltage regulator will operate the LEDs more efficiently. In addition to the current IR thermometer sensor, the NIR wand may have a red guiding light located between the two NIR LEDs so that the lens-focused NIR illumination beams can be visualized. The power consumption of the IR thermometer and guiding LED are less than 30 mA, and the sizes are small enough to be embedded in the LED board. The feedback signal for the temperature alert can be included. Color change on a LED indicator, an alarm, or a tactile signal can tell the user when the temperature has been reached.

TABLE 5

Power consumption calculation. General operating parameters, LED driving conditions, NIR optical power, and possible battery-powered plan are presented.

| Operating parameters | | |
| --- | --- | --- |
| Illumination area | 25.4 × 5 | w × h (mm × mm) |
| # of LED in wand | 4 | (each) |
| Release temperature | 45 | (° C.) |
| Example tape size | 25.4 × 50 | w × h (mm × mm) |
| Time for single tape removal | 5 | (s) |
| LED driving parameters | | |
| Rated current | 1.3 | (A) |
| Rated voltage | 2.8 | (V) |
| Required electrical power | 3.640 | (W) |
| Estimated optical power | 1.885 | (W) |
| NIR illumination | | |
| Required optical power | 1.880 | (W) |
| Required optical intensity | 1.481 | (W/cm$^2$) |
| Single 18650 battery | | |
| Rated capacity | 2500 | (mAh) |
| Continuous running time | 115.4 | (min) |
| Tape removal cycle | 1384 | (cycle) |
| Double 18650 batteries | | |
| Rated capacity | 5000 | (mAh) |
| Continuous running time | 230.8 | (min) |
| Tape removal cycle | 2769 | (cycle) |

FIGS. 3A and 3B show the three-dimensional rendering of the double-battery powered model of an embodiment of the NIR wand using a single row of 4 NIR LEDs with a central red LED. The visible red LED will illuminate the target so the operator can easily see the NIR exposure area. A diffuser and reflector will uniformly focus the illumination from the 4 NIR LEDs.

Skin Safety

Based on the previous in vitro and in vivo studies, the perception of skin pain in adult occurs at skin temperatures above 43° C., and thermal damage occurs when the temperature of the basal layer (the innermost layer of epidermis) reaches 44° C. The dependence of skin pain and injury on the temperature and duration of exposure is commonly accepted. Durations of exposure to induce reversible thermal skin damage have been reported as 45 min at 46.5° C., 60 min at 44° C., and 50 min at 46° C.

According to the ASTM guide C1055-99, epidermis damage (first-degree burns, reversible with no permanent damage) occurs approximately 44° C. after 6 h of thermal contact, and the exposure time to skin damage is reduced by 50% for each 1° C. increase, up to around 51° C. The guideline also included the recommendation of a 1 min exposure limit for infants, elderly, or infirmed, who have slow reaction times. An independent study by Diller presents a specific suggestion for the maximum delivery temperature of domestic tap water, of which a safety standard was based on adult skin thickness. Diller found that the skin thickness ratio between a child and adult is 0.72 and showed the skin injury induced by 10 s of exposure to hot water at 48.9° C. corresponds to the same exposure at 46.7° C. with a child. Exposure to hot water may result in a worse burn injury than the NIR exposure, in which a relatively small area is covered. Thus, safety guidelines and in vitro/vivo studies imply that the UnTape removal process, which increases the temperature of the UnTape adhesive to 45° C. for 1-5 s in the local skin area, would not result in any skin burn.

CONCLUSION

A prototype photothermal tape release system was demonstrated using NIR LEDs and temperature switching high-tack adhesive tape coated with an NIR absorbing dye. This combination of an optical energy source coupled to a matched light absorption coating provided a test bed for forecasting the feasibility of developing a clinically useful system that will lower the incidence of medical adhesive-related skin injuries. Reasonable agreement between the experimentally measured results and a numerical model provides a sound foundation for the design of a next generation UnTape system.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

The embodiments of the invention in which an exclusive property or privilege is claimed are defined as follows:

1. An apparatus for activating a low-adhesion state of a thermal-sensitive tape, the apparatus comprising:
    a light source configured to illuminate a target area of the thermal-sensitive tape with a first spectrum of electromagnetic radiation to provide heating of the target area, wherein the first spectrum includes a first wavelength outside of a visible spectrum; and
    a temperature sensor configured to detect a second spectrum of electromagnetic radiation to approximate a temperature of the target area, and wherein the second spectrum includes a second wavelength different than the first wavelength.

2. The apparatus of claim 1, further comprising:
    an indicator light configured to illuminate the target area with a third spectrum of electromagnetic radiation to visually indicate a location of the heating, wherein the third spectrum includes a third wavelength within the visible spectrum different from the second wavelength.

3. The apparatus of claim 2, wherein full width at half maximum of the first spectrum, the second spectrum, and the third spectrum do not overlap one another within an electromagnetic spectrum.

4. The apparatus of claim 2, wherein the first spectrum is between 750 nm and 1750 nm, wherein the second spectrum is between 5 μm and 14 μm, and wherein the third spectrum is between 400 nm and 700 nm.

5. The apparatus of claim 2, wherein the first spectrum is between 750 nm and 1750 nm, the second spectrum is between 5 μm and 14 μm, or the third spectrum is between 400 nm and 700 nm.

6. The apparatus of claim 1, wherein the first spectrum is between 750 nm and 1750 nm or the second spectrum is between 5 μm and 14 μm.

7. The apparatus of claim 1, wherein the thermal-sensitive tape includes a photosensitive absorber capable of absorbing incident light within a first absorption spectrum of electromagnetic radiation, wherein the first spectrum overlaps, at least in part, with the first absorption spectrum such that the temperature of the target area is based, at least in part, on an intensity of the first spectrum output by the light source when the light source is illuminating the target area, and wherein adhesive strength of the thermal-sensitive tape at the target area is based on the temperature of the target area.

8. The apparatus of claim 1, further comprising a controller coupled to the light source and the temperature sensor, and wherein the controller includes logic that when executed by the controller causes the apparatus to perform operations including:
    illuminating the target area with the first spectrum to heat the target area of the thermal-sensitive tape to within a thermal release temperature range;
    monitoring the temperature of the target area with the temperature sensor to provide temperature feedback; and
    adjusting an intensity of the first spectrum based on the temperature feedback to maintain the temperature of the target area within the thermal release temperature range without exceeding a first threshold temperature.

9. The apparatus of claim 8, wherein the thermal-sensitive tape is adhered to an object, and wherein the controller includes additional logic that when executed by the controller causes the apparatus to perform further operations including:
    estimating a temperature of the object based, at least in part, on an expected heat flux of the thermal-sensitive tape; and
    reducing the temperature of the target area to prevent the estimated temperature of the object from reaching a second threshold temperature.

10. The apparatus of claim 9, wherein the controller includes additional logic that when executed by the controller causes the apparatus to perform further operations including:
    reducing the intensity of the first spectrum to reduce the temperature of the target area, and wherein preventing the estimated temperature of the object from reaching the second threshold is prioritized over maintaining the temperature of the target area within the thermal release temperature range.

11. The apparatus of claim 10, wherein the first threshold temperature is different than the second threshold temperature.

12. The apparatus of claim 8, further comprising:
an indicator light configured to illuminate the target area with a third spectrum of electromagnetic radiation to visually indicate a location of the heating, wherein the third spectrum includes a third wavelength within the visible spectrum different from the second spectrum, wherein the indicator light includes a first light emitting diode of a first color and a second light emitting diode of a second color, and wherein the first color is different from the second color.

13. The apparatus of claim 12, wherein the controller includes additional logic that when executed by the controller causes the apparatus to perform further operations including:
illuminating the target area with the first color, including the third wavelength, when the temperature of the target area is less than the thermal release temperature range; and
illuminating the target area with the second color when the temperature of the target area is within the thermal release temperature range to provide feedback that the thermal-sensitive tape proximate to the target area is in a low adhesion state.

14. The apparatus of claim 13, wherein the controller includes additional logic that when executed by the controller causes the apparatus to perform further operations including ending the illuminating of the target area with the first color when the temperature of the target area is within the thermal release temperature range.

15. The apparatus of claim 8, wherein the controller includes additional logic that when executed by the controller causes the apparatus to perform further operations including providing at least one of visual feedback, tactile feedback, or audible feedback to a user of the apparatus to indicate that the temperature of the target area is within the thermal release temperature range.

16. The apparatus of claim 8, further comprising an input device coupled to the controller and configurable to adjust the first threshold temperature based on a user preference.

17. The apparatus of claim 8, wherein the light source includes a plurality of first light emitting diodes (LEDs) and the temperature sensor includes a plurality of pyrometers, and wherein the plurality of first LEDs and the plurality of pyrometers are arranged to variably illuminate different zones of the target area and determine the temperature of each of the different zones of the target area.

18. The apparatus of claim 17, wherein the temperature feedback provides temperature information for each of the different zones, and wherein the intensity of the first spectrum is adjustable to provide substantially uniform heating of the different zones based on the temperature information.

19. The apparatus of claim 17, further comprising an indicator light configured to illuminate the target area with a third spectrum of electromagnetic radiation to visually indicate a location of the heating, wherein the third spectrum includes a third wavelength within the visible spectrum different from the second spectrum, wherein the indicator light includes a plurality of second LEDs, and wherein the plurality of second LEDs are arranged proximate to the plurality of first LEDs to visually define at least a perimeter boundary of the plurality of first LEDs when the light source and the indicator light are simultaneously illuminating the target area.

20. The apparatus of claim 19, wherein the plurality of second LEDs includes a at least a first laser diode and a second laser diode offset from the first laser diode such that electromagnetic emission of the first laser diode and the second laser diode overlap on the target area when the apparatus is at a pre-determined distance from the target area.

21. The apparatus of claim 19, wherein the plurality of first LEDS are arranged as a linear array interspersed with the plurality of second LEDs.

22. A system, comprising:
a thermal-sensitive tape including a photosensitive absorber that absorbs incident light within a first absorption spectrum of electromagnetic radiation, wherein adhesive strength of a target area of the thermal-sensitive tape is based on a temperature of the target area;
an apparatus configurable to illuminate the target area of the thermal-sensitive tape, the apparatus including:
a light source configured to illuminate the target area of the thermal-sensitive tape with a first spectrum of electromagnetic radiation to provide heating of the target area, wherein the first spectrum includes a first wavelength outside of a visible spectrum, wherein the first spectrum overlaps, at least in part, with the first absorption spectrum such that the temperature of the target area is based, at least in part, on an intensity of the first spectrum output by the light source when the light source is illuminating the target area;
a temperature sensor configured to detect a second spectrum of electromagnetic radiation to approximate the temperature of the target area, and wherein the second spectrum includes a second wavelength different than the first wavelength; and
an indicator light configured to illuminate the target area with a third spectrum of electromagnetic radiation to visually indicate a location of the heating, wherein the third spectrum includes a third wavelength within the visible spectrum.

23. The system of claim 22, wherein the apparatus further comprises:
a controller coupled to the light source, the indicator light, and the temperature sensor, and wherein the controller includes logic that when executed by the controller causes the apparatus to perform operations including:
illuminating the target area with the first spectrum to heat the target area of the thermal-sensitive tape to within a thermal release temperature range;
monitoring the temperature of the target area with the temperature sensor to provide temperature feedback; and
adjusting the intensity of the first spectrum based on the temperature feedback to maintain the temperature of the target area within the thermal release temperature range without exceeding a first threshold temperature.

24. A method for activating a low-adhesion state of a thermal-sensitive tape, the method comprising:
illuminating a target area of the thermal-sensitive tape with a first spectrum of electromagnetic radiation to provide heating of the target area of the thermal-sensitive tape to within a thermal release temperature range, wherein the first spectrum includes a first wavelength outside of a visible spectrum;
monitoring a temperature of the target area by detecting a second spectrum of electromagnetic radiation emitted by the thermal-sensitive tape to provide temperature feedback;
illuminating the target area of the thermal-sensitive tape with a third spectrum of electromagnetic radiation to visually indicate a location of the heating, wherein the third spectrum includes a third wavelength within the visible spectrum; and adjusting an intensity of the first spectrum based on the temperature feedback to maintain the temperature of the target area within the thermal release temperature range without exceeding a first threshold temperature.

25. The method of claim 24, further comprising:

estimating a temperature of an object underlying the target area of the thermal-sensitive tape based, at least in part, on an expected heat flux of the thermal-sensitive tape; and reducing the temperature of the target area to prevent the estimated temperature of the object from reaching a second threshold.

26. The method of claim 25, further comprising:

illuminating the target area with a first color of the third spectrum, including the third wavelength, when the temperature of the target area is less than the thermal release temperature range; and illuminating the target area with a second color of the third spectrum when the temperature of the target area is within the thermal release temperature range to provide feedback that the thermal-sensitive tape proximate to the target area is in a low adhesion state.

27. The apparatus of claim 1, wherein the first spectrum is between 750 nm and 1750 nm and wherein the second spectrum is between 5 μm and 14 μm.

* * * * *